(12) United States Patent
Li et al.

(10) Patent No.: US 10,196,411 B2
(45) Date of Patent: Feb. 5, 2019

(54) TIZOXANIDE PHOSPHATE AND ALKANE SULFONATE AND PHARMACEUTICAL APPLICATIONS THEREOF

(71) Applicant: Institute of Pharmacology and Toxicology Academy of Military Medical Sciences P.L.A. China, Beijing (CN)

(72) Inventors: Song Li, Beijing (CN); Xingzhou Li, Beijing (CN); Wu Zhong, Beijing (CN); Zhibing Zheng, Beijing (CN); Junhai Xiao, Beijing (CN); Xinbo Zhou, Beijing (CN); Yunde Xie, Beijing (CN); Xiaokui Wang, Beijing (CN); Lili Wang, Beijing (CN); Wei Chen, Beijing (CN); Fei Xie, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/539,266

(22) PCT Filed: Dec. 11, 2015

(86) PCT No.: PCT/CN2015/097074
§ 371 (c)(1),
(2) Date: Jun. 23, 2017

(87) PCT Pub. No.: WO2016/101794
PCT Pub. Date: Jun. 30, 2016

(65) Prior Publication Data
US 2017/0362261 A1    Dec. 21, 2017

(30) Foreign Application Priority Data

Dec. 23, 2014  (CN) .......................... 2014 1 0808939

(51) Int. Cl.
| | |
|---|---|
| *C07D 277/58* | (2006.01) |
| *C07F 9/6539* | (2006.01) |
| *A61K 31/426* | (2006.01) |
| *A61K 31/675* | (2006.01) |
| *A61P 31/20* | (2006.01) |
| *A61P 31/14* | (2006.01) |
| *A61P 31/16* | (2006.01) |
| *A61P 31/06* | (2006.01) |
| *A61P 33/02* | (2006.01) |
| *A61P 33/04* | (2006.01) |
| *A61P 33/10* | (2006.01) |
| *A61P 1/00* | (2006.01) |

(52) U.S. Cl.
CPC .......... *C07F 9/6539* (2013.01); *A61K 31/426* (2013.01); *A61K 31/675* (2013.01); *C07D 277/58* (2013.01); *Y02A 50/409* (2018.01); *Y02A 50/488* (2018.01); *Y02A 50/49* (2018.01); *Y02A 50/491* (2018.01)

(58) Field of Classification Search
CPC .. C07D 277/28; C07D 277/58; A61K 31/426; A61K 31/675; C07F 9/6539
USPC .................................. 548/190, 192; 514/371
See application file for complete search history.

(56) References Cited

U.S. PATENT DOCUMENTS

| | | | |
|---|---|---|---|
| 4,315,018 A | 2/1982 | Rossignol | |
| 5,935,591 A | 8/1999 | Rossignol et al. | |
| 8,124,632 B2* | 2/2012 | Rossignol ............ | C07D 417/12 514/369 |
| 2006/0094817 A1 | 5/2006 | Muto | |
| 2009/0036467 A1 | 2/2009 | Rossignol et al. | |
| 2012/0122939 A1 | 5/2012 | Rossignol et al. | |

FOREIGN PATENT DOCUMENTS

| | | |
|---|---|---|
| CN | 1658855 A | 8/2005 |
| CN | 101835765 A | 9/2010 |
| CN | 102335171 A | 2/2012 |

OTHER PUBLICATIONS

Theuretzbacher et al. Current Opinion in Pharmacology, 2011,11: 429-432.*
Bassetti et al. Annals of Clinical Microbiology and Antimicrobials 2013, 12:22, pp. 1-15.*
Shaffer R. K. Yale Journal of Biology and Medicine 86 (2013), pp. 261-270.*

(Continued)

*Primary Examiner* — Venkataraman Balasubramanian
(74) *Attorney, Agent, or Firm* — Sterne, Kessler, Goldstein & Fox P.L.L.C.

(57) ABSTRACT

The invention relates to tizoxanide phosphate or alkane sulfonate compounds represented by Formula I, and pharmaceutically acceptable salts thereof, isomers thereof, hydrates thereof or solvates thereof, and pharmaceutical applications of the compounds.

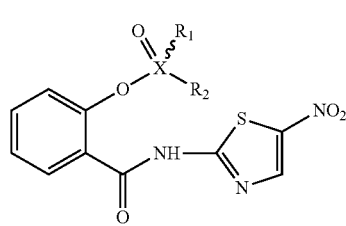

18 Claims, 1 Drawing Sheet

(56) References Cited

OTHER PUBLICATIONS

Kint et al. Trends in Microbiology, Dec. 2012, vol. 20, No. 12, 577-585.*

Becker D.E. Anesth Prog 60:111-123, Jul. 2013.*

"First Office Action," for CN Appl. No. 201410808939.0, dated Apr. 28, 2017 by the State Intellectual Property Office of the People's Republic of China, Beijing, CN.

"The Second Office Action," for CN Appl. No. 201410808939.0, dated Sep. 13, 2017 by the State Intellectual Property Office of the People's Republic of China, Beijing, CN.

International Search Report (ISR) for PCT/CN2015/097074; I.A. fd: Dec. 11, 2015, dated Mar. 17, 2016, State Intellectual Property Office of the P.R. China, Beijing, China.

International Preliminary Report on Patentability (IPRP) (Chapter I of the Patent Cooperation Treaty) (PCT Rule 44bis) for PCT/CN2015/097074; I.A. fd: Dec. 11, 2015; dated Jun. 27, 2017, by The International Bureau of WIPO, Geneva, Switzerland.

NDA Application No. 21-818 and 21-498/S-003, submitted Dec. 21, 2004, for Nitazoxanide 500 mg tablets and Oral Suspension, Romark Laboratories, L.C., Applicant; Dakshina Chilukuri, Reviewer; Type of Submission: NDA Resubmission and efficacy supplement; Review Date: Jun. 10, 2005; and NDA Application No. 21-497 and 21-498, submitted Dec. 21, 2004, for Nitazoxanide, Romark Laboratories, L.C., Applicant; Dakshina Chilukuri, Reviewer; Type of Submission: NDA; Review Date: Oct. 4, 2002; Clinical Pharmacology and Biopharmaceutics Review(s), Center for Drug Evaluation and Research, Office of Clinical Pharmacology and Biopharmaceutics Review, Approval Jun. 16, 2005 (pp. 1-39).

Fox, LM et al., "Nitazoxanide: a new thiazolide antiparasitic agent," Clin Infect Dis. Apr. 15, 2005;40(8):1173-80. Epub Mar. 14, 2005.

Gilles, HM et al., "Treatment of intestinal parasitic infections: a review of nitazoxanide," Trends Parasitol. Mar. 2002;18(3):95-7.

Rossignol, JA et al., "Treatment of diarrhea caused by *Cryptosporidium parvum*: a prospective randomized, double-blind, placebo-controlled study of Nitazoxanide," J Infect Dis. Jul. 1, 2001;184(1):103-6. Epub May 29, 2001.

Gupta, S et al., "Nitazoxanide: Broad Spectrum Anti-Protozoal," Journal of Medical Education and Research 8(1), Jan.-Mar. 2006, pp. 60-61, JK Science.

Korba, BE et al., "Nitazoxanide, tizoxanide and other thiazolides are potent inhibitors of hepatitis B virus and hepatitis C virus replication," Antiviral Res. Jan. 2008;77(1):56-63. Epub Sep. 4, 2007.

Korba, B et al., "Nitazoxanide is an effective antiviral agent against both HBV and HCV replication in vitro," Program and Abstracts/Antiviral Research (Jun. 2007) Abstract No. 31, p. A40, Abstracts of the 20th International Conference on Antiviral Research (ICAR), Apr. 29-May 3, 2007, Palm Springs, California, USA., doi:10.1016/j.antiviral.2007.01.039.

Darling, JM et al., "Nitazoxanide: beyond parasites toward a novel agent for hepatitis C," Gastroenterology. Mar. 2009;136(3):760-3. doi: 10.1053/j.gastro.2009.01.020. Epub Jan. 22, 2009.

Belardo, G et al., "Nitazoxanide, a Novel Potential Anti-Influenza Drug, Acting in Synergism with Neuraminidase Inhibitors," poster presented at the IDSA 2011 Poster Abstract Session: New Approaches to Anti-Viral Therapy, Saturday, Oct. 22, 2011; Infectious Diseases Society of America (IDSA) Annual Meeting, Oct. 20-23, 2011 Boston, MA.

Rossignol, JF et al., "Thiazolides, a new class of anti-influenza molecules targeting viral hemagglutinin at the post-translational level," J Biol Chem. Oct. 23, 2009;284(43):29798-808. doi: 10.1074/jbc.M109.029470. Epub Jul. 28, 2009, ASBMB, Baltimore, MD.

Ashton, Laura V. et al. "In Vitro Susceptibility of Canine Influenza A (H3N8) Virus to Nitazoxanide and Tizoxanide," Veterinary Medicine International 2010 (2010): Article ID:891010. PMC. Jun. 29, 2018, 5 pages, doi:10.4061/2010/891010.

Siddiq, DM et al, "Norovirus gastroenteritis successfully treated with nitazoxanide," J Infect. Nov. 2011;63(5):394-7. doi: 10.1016/j.jinf.2011.08.002. Epub Aug. 9, 2011.

Musher, DM et al., "Nitazoxanide versus vancomycin in Clostridium difficile infection: a randomized, double-blind study," Clin Infect Dis. Feb. 15, 2009;48(4):e41-6. doi: 10.1086/596552.

Shigyo, K et al., "Efficacy of nitazoxanide against clinical isolates of *Mycobacterium tuberculosis*," Antimicrob Agents Chemother. Jun. 2013;57(6):2834-7. doi: 10.1128/AAC.02542-12. Epub Mar. 18, 2013.

de Carvalho, LP et al., "Nitazoxanide kills replicating and nonreplicating *Mycobacterium tuberculosis* and evades resistance," J Med Chem. Oct. 8, 2009;52(19):5789-92. doi: 10.1021/jm9010719.

Mégraud, F et al., Nitazoxanide, a potential drug for eradication of Helicobacter pylori with no cross-resistance to metronidazole, Antimicrob Agents Chemother. Nov. 1998;42(11):2836-40.

Ramos-Soriano, AG et al., "Nitazoxanide Use as Part of an Empiric Multi-Drug Regimen in Treating Children with Suspected Helicobacter pylori Infection," Case Rep Gastroenterol. Jan. 27, 2015;9(1):36-42. doi: 10.1159/000375116. eCollection Jan.-Apr. 2015.

Tchouaffi-Nana, F. et al., "Nitazoxanide inhibits biofilm formation by *Staphylococcus epidermidis* by blocking accumulation on surfaces," Antimicrob Agents Chemother. Jul. 2010;54(7):2767-74. doi: 10.1128/AAC.00901-09. Epub Apr. 19, 2010.

Shamir, ER et al., "Nitazoxanide inhibits biofilm production and hemagglutination by enteroaggregative *Escherichia coli* strains by blocking assembly of AafA fimbriae," Antimicrob Agents Chemother. Apr. 2010;54(4):1526-33. doi: 10.1128/AAC.01279-09. Epub Jan. 19, 2010.

Extended European search report for EP application No. 15871863.5, including the supplementary European search report and the European search opinion, dated Jun. 21, 2018, The European Patent Office, Munich, Germany.

* cited by examiner

TIZOXANIDE PHOSPHATE AND ALKANE SULFONATE AND PHARMACEUTICAL APPLICATIONS THEREOF

TECHNICAL FIELD

The invention relates to tizoxanide phosphate or alkane sulfonate compounds and pharmaceutically acceptable salts thereof, isomers thereof, hydrates thereof or solvates thereof, as well as pharmaceutical applications of the compounds.

BACKGROUND ART

Nitazoxanide (NTZ), which is a thiazolyl benzamide compound developed by Romark Laboratory, has multiple bioactivities. NTZ has a chemical name of "2-acetoxy-N-(5-nitro-2-thiazolyl)benzamide", a chemical formula of $C_{12}H_9N_3O_5S$, and a melting point of 202° C., and is a light yellow powder, which is insoluble in water, slightly soluble in ethanol, and soluble in organic solvents such as tetrahydrofuran, dimethyl sulfoxide (DMSO) and N,N-dimethylformamide (DMF).

Studies have shown that nitazoxanide is effective in combating a variety of parasites in human such as protozoan and helminth, specifically including: *Giardia, Amoeba, Cryptosporidium, Cyclospora, Trichomonad, Encephalitozoon intestinalis, Isospora Blastocystis hominis, Balantidium coli, Ascaris lumbricoides, Enterocytozoon bieneusi,* Tapeworm (including *Taenia saginata, Hymenolepis nana*), *Diplacanthus nanus, Giardia Leishmania, Fasciola hepatica,* etc. Nitazoxanide has good therapeutic effect on viral infectious diseases such as hepatitis B (HBV), hepatitis C (HCV), influenza (including canine influenza), and viral enterogastritis caused by Rotavirus or Norovirus. Nitazoxanide is also useful in combating infection caused by bacteria such as *Clostridium difficile* (CD), *Tubercle bacillus* (including drug-resistant *Tubercle bacillus*) and *Helicobacter pylori,* and also has a good inhibitory effect on the biofilm formation caused by bacteria.

Nitazoxanide is a prodrug which is quickly hydrolyzed to its active metabolite tizoxanide (TIZ) in vivo after administration. The pharmacokinetic studies in human show that after oral administration, nitazoxanide is absorbed by gastrointestinal tract, wherein about ⅓ of the oral dose is excreted by urine, and about ⅔ of the oral dose is excreted by feces. In blood, nitazoxanide is quickly metabolized by plasma esterase (the half-life is about 6 min at 37° C.), and is deacetylated by hydrolysis to produce its active metabolite tizoxanide. Therefore, nitazoxanide is not detectable in plasma, urine, bile and feces. Tizoxanide can be further subjected to glucuronidation in vivo to produce tizoxanide glucuronide having no pharmaceutical activity. Tizoxanide is present in plasma, urine, bile and feces, and tizoxanide glucuronide is also present in plasma, urine and bile.

Nitazoxanide has good pharmaceutical properties such as multiple bioactivities and good safety, but also has some obvious disadvantages, which mainly reside in the following two aspects.

(1) Nitazoxanide has the shortcomings such as low bioavailability, short half life, and low blood concentration. It is found by Pharmacokinetic Laboratory of Institute of pharmacology & Toxicology Academy of Military Medical Sciences that when nitazoxanide suspension was orally administered to rats, the absolute bioavailability was only 7.2%. In addition, it is reported in papers that when nitazoxanide was orally administered to healthy adults, after single administration of 500 mg, the active metabolite tizoxanide had a time to peak ($T_{max}$) of 3-4 h, a AUC value of about 3.9-11.3 μg*h/mL, a maximum concentration ($C_{max}$) of 1.9 μg/mL (in the range of 1.1-2.5), and a short half life of only from 1.03 to 1.6 h.

(2) Nitazoxanide has relatively low activity, for example, nitazoxanide has a minimal inhibitory concentration (MIC) of from 12 to 28 μg/mL (the median value is 16 μg/mL) for *Mycobacterium tuberculosis;* nitazoxanide and tizoxanide have the minimal inhibitory concentrations (MICs) of between 0.25 and 8 μg/mL, the 50% minimal inhibitory concentration ($MIC_{50}$) of 1 μg/mL, and the 90% minimal inhibitory concentration ($MIC_{90}$) of 4 μg/mL for 103 strains of *Helicobacter pylori;* under aerobic or microaerophilic conditions, nitazoxanide and tizoxanide have a minimal inhibitory concentration (MIC) of 8~16 μg/mL for *Staphylococcus epidermidis* or other *Staphylococcus* (including methicillin resistant *Staphylococcus aureus*); nitazoxanide has an $EC_{50}$ of 1 μg/mL and an $EC_{90}$ of 7 μg/mL for PR8 influenza virus in MDCK cells.

As can be seen, nitazoxanide has the shortcomings of low bioavailability, short half life, and low blood concentration. When nitazoxanide is used in the treatment of infections by parasites such as intestinal protozoans and helminths, nitazoxanide can work without entering blood. Therefore, the properties of nitazoxanide, i.e., poor oral absorption, low bioavailability, and low blood concentration, would not influence its therapeutic effect on the treatment of infections by parasites such as intestinal protozoans and helminths. However, if nitazoxanide is applied to the treatment of drug-resistant *Tubercle bacillus, Helicobacter pylori* or methicillin resistant *Staphylococcus aureus,* or the treatment of viral infectious diseases caused by influenza virus, Rotavirus and the like, the blood concentration should be at least higher than the minimal inhibitory concentration (MIC) or the minimal effective concentration. The shortcomings of nitazoxanide, i.e., poor oral absorption, low bioavailability, and low blood concentration, are necessarily observed and directly influence its pharmaceutical effect.

Therefore, if nitazoxanide agent is applied to the treatment of drug-resistant *tubercle bacillus, Helicobacter pylori* or methicillin resistant *Staphylococcus aureus,* or the treatment of viral infectious diseases caused by influenza virus, Rotavirus and the like, it will be necessary to enhance the bioavailability, increase the blood concentration, and prolong the half life of nitazoxanide calculated as tizoxanide, so as to have therapeutic effects such as anti-bacterial and anti-viral effects.

CONTENTS OF INVENTION

The inventor of the invention surprisingly found that when tizoxanide as a parent compound is modified to a tizoxanide phosphate or alkane sulfonate derivative, calculated as tizoxanide, the oral administration of which can effectively improve the bioavailability, increase the blood concentration, and prolong the half-life, thereby improving the therapeutic effects of the drug, such as anti-bacterial and anti-viral effects. Some compounds can also enhance water solubility significantly, and can be prepared into liquid preparations of solutions for use in intramuscular injection or intravenous injection, which greatly improve the bioavailability and the blood concentration calculated as tizoxanide.

The invention provides a classes of tizoxanide phosphate or alkane sulfonate compounds, which can be converted into the form of tizoxanide in vivo so as to exert an action against protozoans, helminths, viruses or bacteria, and meanwhile significantly improve the bioavailability and the blood concentration calculated as tizoxanide, retain the effective blood concentration for a longer time, and make the blood concentration curve more stable.

In the first aspect, the invention relates to a tizoxanide phosphate or alkane sulfonate compound of Formula I, or a pharmaceutically acceptable salt, an isomer, a hydrate or a solvate thereof,

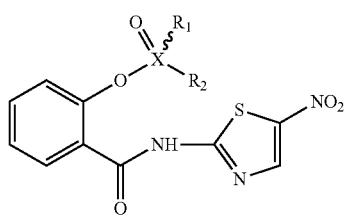

I wherein: X=P or S, when X=P, " $\sim$ " represents a single bond, $R_1$ and $R_2$ each are independently hydroxyl or $C_{1-6}$alkoxy, said $C_{1-6}$alkoxy is optionally substituted by 1-2 substituents independently selected from the group consisting of: aryl, amino, hydroxyl, cyano, nitro, $C_{1-4}$alkyl and halogen (e.g., F, Cl, Br or I), said aryl is optionally substituted by 1-2 substituents independently selected from the group consisting of: amino, hydroxyl, cyano, nitro, $C_{1-4}$alkyl and halogen (e.g., F, Cl, Br or I); or when X=S, " $\sim$ " represents a double bond, $R_1$ is O, $R_2$ is $C_{1-6}$alkyl or aryl, said $C_{1-6}$alkyl or aryl is optionally substituted by 1-2 substituents independently selected from the group consisting of: amino, hydroxyl, cyano, nitro, $C_{1-4}$alkyl, halogen (e.g., F, Cl, Br or I) and tert-butoxycarbonylamino.

In an embodiment, the compound of Formula I, or a pharmaceutically acceptable salt, an isomer, a hydrate or a solvate thereof according to the first aspect of the invention, wherein, When X=P, " $\sim$ " represents a single bond, $R_1$ and $R_2$ each are independently hydroxyl or $C_{1-4}$alkoxy, said $C_{1-4}$alkoxy is optionally substituted by 1-2 substituents independently selected from the group consisting of: phenyl, amino, hydroxyl, cyano, nitro, $C_{1-4}$alkyl, and halogen (e.g., F, Cl, Br or I), said phenyl is optionally substituted by 1-2 substituents independently selected from the group consisting of: amino, hydroxyl, cyano, nitro, $C_{1-4}$alkyl, and halogen (e.g., F, Cl, Br or I); or when X=S, " $\sim$ " represents a double bond, $R_1$ is O, $R_2$ is $C_{1-4}$alkyl or phenyl, said $C_{1-4}$alkyl or phenyl is optionally substituted by 1-2 substituents independently selected from the group consisting of: amino, hydroxyl, cyano, nitro, $C_{1-4}$alkyl, halogen (e.g., F, Cl, Br or I), tert-butoxycarbonylamino.

In another embodiment, the compound of Formula I, or a pharmaceutically acceptable salt, an isomer, a hydrate or a solvate thereof according to the first aspect of the invention, wherein, when X=P, " $\sim$ " represents a single bond, $R_1$ and $R_2$ each are independently selected from the group consisting of hydroxyl, methoxy, ethoxy, n-propoxy, isopropoxy, n-butoxy, sec-butoxy, isobutoxy, tert-butoxy, benzyloxy, phenylethoxy, 1-phenylpropoxy, 1-phenylbutoxy, fluoromethoxy, difluoromethoxy, trifluoromethoxy, chloromethoxy, dichloromethoxy, trichloromethyl, aminomethoxy, aminoethoxy, hydroxylmethoxy, hydroxylethoxy, nitromethoxy and nitroethoxy; or when X=S, " $\sim$ " represents a double bond, $R_1$ is O, $R_2$ is selected from the group consisting of methyl, ethyl, n-propyl, isopropyl, n-butyl, sec-butyl, isobutyl, tert-butyl, phenyl, fluoromethyl, difluoromethyl, trifluoromethyl, chloromethyl, dichloromethyl, trichloromethyl, p-methylphenyl, m-methylphenyl, o-methylphenyl, aminomethyl, aminoethyl, hydroxylmethyl, hydroxylmethyl, nitromethyl, nitroethyl, tert-butoxycarbonylaminomethyl and tert-butoxycarbonylaminoethyl.

In another embodiment, the compound of Formula I, or a pharmaceutically acceptable salt, an isomer, a hydrate or a solvate thereof according to the first aspect of the invention, wherein, when X=P, " $\sim$ " represents a single bond, $R_1$ and $R_2$ each are independently selected from the group consisting of hydroxyl, methoxy, ethoxy and benzyloxy; or when X=S, " $\sim$ " represents a double bond, $R_1$ is O, and $R_2$ is selected from the group consisting of methyl, ethyl, n-propyl, n-butyl, p-methylphenyl and aminoethyl.

In another embodiment, the compound of Formula I, or a pharmaceutically acceptable salt, an isomer, a hydrate or a solvate thereof according to the first aspect of the invention, wherein, when X=P, " $\sim$ " represents a single bond, $R_1$ and $R_2$ each are independently selected from the group consisting of hydroxyl, methoxy and ethoxy; or when X=S, " $\sim$ " represents a double bond, $R_1$ is O, and $R_2$ is selected from the group consisting of methyl, ethyl, n-propyl, n-butyl and aminoethyl.

In another embodiment, the compound of Formula I, or a pharmaceutically acceptable salt, an isomer, a hydrate or a solvate thereof according to the first aspect of the invention, wherein, when X=P, " $\sim$ " represents a single bond, $R_1$ and $R_2$ are the same substituent, selected from the group consisting of hydroxyl, methoxy and ethoxy; or when X=S, " $\sim$ " represents a double bond, $R_1$ is O, and $R_2$ is selected from the group consisting of methyl, ethyl, n-propyl, n-butyl and aminoethyl.

In another embodiment, the compound of Formula I, or a pharmaceutically acceptable salt, an isomer, a hydrate or a solvate thereof according to the first aspect of the invention, wherein, X=P, " $\sim$ " represents a single bond, $R_1$ and $R_2$ are the same substituent, selected from the group consisting of hydroxyl, methoxy and ethoxy.

In another embodiment, the compound of Formula I, or a pharmaceutically acceptable salt, an isomer, a hydrate or a solvate thereof according to the first aspect of the invention, wherein, X=S, " $\sim$ " represents a double bond, $R_1$ is O, and $R_2$ is selected from the group consisting of methyl, ethyl, n-propyl, n-butyl and aminoethyl.

In another embodiment, the compound of Formula I, or a pharmaceutically acceptable salt, an isomer, a hydrate or a solvate thereof according to the first aspect of the invention, wherein, when X=P, said pharmaceutically acceptable salt is an addition salt formed by the compound of Formula I and a suitable base, such as monosodium salt, disodium salt, calcium salt, monopotassium salt, dipotassium salt, or meglumine salt; or when X=S, said pharmaceutically acceptable salt is an addition salt formed by the compound of Formula I and a suitable acid, such as hydrochlorate, sulphurate, acetate, or nitrate.

In a preferred embodiment, said suitable base may be an organic base or an inorganic base, such as sodium hydroxide, potassium hydroxide, calcium hydroxide, calcium acetate, or meglumine. For example, said pharmaceutically acceptable salt of the compound of Formula I is a monosodium salt, disodium salt, calcium salt, monopotassium salt, dipotassium salt, or meglumine salt of the compound of Formula I. For example, when X=P, said pharmaceutically acceptable salt is a monosodium salt, disodium salt, calcium salt, monopotassium salt, dipotassium salt, or meglumine salt of the compound of Formula I.

In another preferred embodiment, said suitable acid may be an organic acid or an inorganic acid, such as hydrochloric acid, sulphuric acid, acetic acid, or nitric acid. For example, said pharmaceutically acceptable salt of the compound of Formula I is a hydrochlorate, a sulphurate, an acetate, or a nitrate of Formula I, preferably a hydrochlorate of the compound of Formula I. For example, when X=S, said pharmaceutically acceptable salt is a hydrochlorate, a sulphurate, an acetate, or a nitrate of the compound of Formula I.

In another embodiment, the compound of Formula I, or a pharmaceutically acceptable salt, an isomer, a hydrate or a solvate thereof according to the first aspect of the invention, is selected from the group consisting of:

Compound 1: dibenzyl 2-(5-nitrothiazol-2-yl-carbamoyl) phenyl phosphate;
Compound 2: 2-(5-nitrothiazol-2-yl-carbamoyl)phenyl dihydrogen phosphate;
Compound 3: 2-(5-nitrothiazol-2-yl-carbamoyl)phenyl hydrogen phosphate monosodium salt;
Compound 4: 2-(5-nitrothiazol-2-yl-carbamoyl)phenyl phosphate disodium salt;
Compound 5: 2-(5-nitrothiazol-2-yl-carbamoyl)phenyl phosphate calcium salt;
Compound 6: 2-(5-nitrothiazol-2-yl-carbamoyl)phenyl methanesulfonate;
Compound 7: 2-(5-nitrothiazol-2-yl-carbamoyl)phenyl ethanesulfonate;
Compound 8: 2-(5-nitrothiazol-2-yl-carbamoyl)phenyl 1-propanesulfonate;
Compound 9: 2-(5-nitrothiazol-2-yl-carbamoyl)phenyl 1-butanesulfonate;
Compound 10: 2-(5-nitrothiazol-2-yl-carbamoyl)phenyl p-toluenesulfonate;
Compound 11: 2-(5-nitrothiazol-2-yl-carbamoyl)phenyl N-BOC-taurate;
Compound 12: 2-(5-nitrothiazol-2-yl-carbamoyl)phenyl taurate hydrochloride;
Compound 13: 2-(5-nitrothiazol-2-yl-carbamoyl)phenyl taurate
Compound 14: 2-(5-nitrothiazol-2-yl-carbamoyl)phenyl hydrogen phosphate monopotassium;
Compound 15: 2-(5-nitrothiazol-2-yl-carbamoyl)phenyl phosphate dipotassium;
Compound 16: 2-(5-nitrothiazol-2-yl-carbamoyl)phenyl hydrogen phosphate meglumine salt;
Compound 17: dimethyl 2-(5-nitrothiazol-2-yl-carbamoyl) phenyl phosphate; and
Compound 18: diethyl 2-(5-nitrothiazol-2-yl-carbamoyl) phenyl phosphate.

In the second aspect, the invention provides a method for preparing the compound of Formula I according to the first aspect of the invention, wherein, when X=P, the method comprises the following steps: in an aprotic solvent (such as dimethylformamide, tetrahydrofuran, or acetonitrile), in the presence of carbon tetrachloride and an organic base (such as triethylamine or diisopropylethylamine), and with dimethylaminopyridine (DMAP) as catalyst, tizoxanide is reacted with a compound of Formula II to obtain the compound of Formula I, and optionally, the compound of Formula I is reacted with a suitable base (such as sodium hydroxide, calcium hydroxide, potassium hydroxide, or meglumine) to form pharmaceutically acceptable salt; or

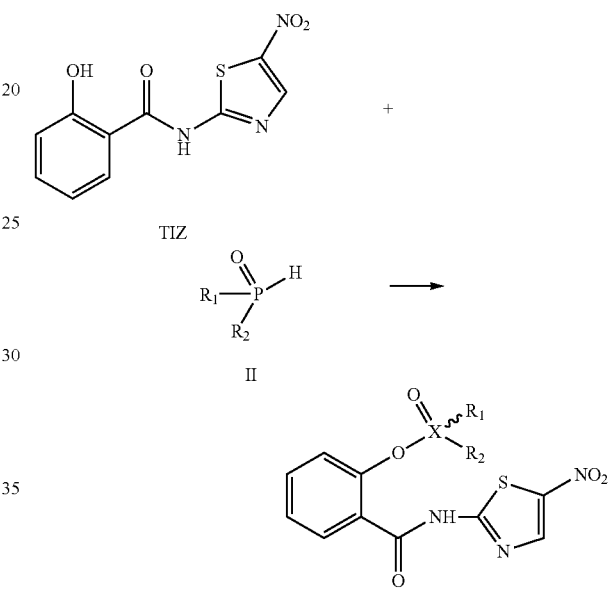

when X=S, the method comprises the following steps: tizoxanide is dissolved or suspended in an aprotic solvent (such as N,N-dimethylformamide, acetonitrile, or tetrahydrofuran), and with an organic base (such as triethylamine, diisopropylethylamine, or 1,8-diazabicyclo[5.4.0]undec-7-ene (DBU)) or an inorganic base (such as sodium carbonate, potassium carbonate, sodium hydride, or sodium bicarbonate) as an acid receptor, is reacted with $R_2$-substituted sulfonyl chloride of Formula III, to obtain the compound of Formula I, and optionally, the compound of Formula I is reacted with a suitable acid (such as hydrochloric acid, sulphuric acid, acetic acid, or nitric acid) to form an addition salt,

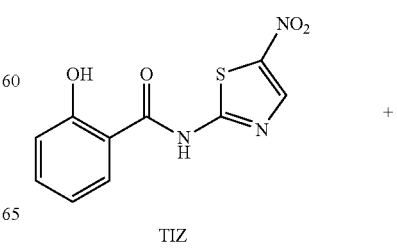

-continued

R₂—SO₂Cl ⟶

III

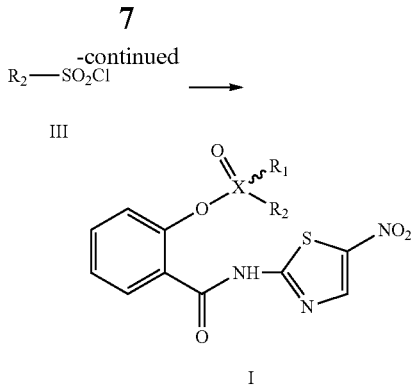

I wherein R₁, R₂ and "~~~" bond have the same meanings as defined in claim 1.

In the third aspect, the invention provides a pharmaceutical composition, comprising the compound of Formula I, or a pharmaceutically acceptable salt, an isomer, a hydrate or a solvate thereof according to the first aspect of the invention.

preferably, said pharmaceutical composition further comprises a pharmaceutically acceptable carrier or excipient; particularly, said pharmaceutical composition is in the form of a solid preparation, an injection, an external preparation, a spray, a liquid preparation, or a compound preparation.

In the fourth aspect, the invention provides use of the pharmaceutical composition according to the third aspect or the compound of Formula. I, or a pharmaceutically acceptable salt, an isomer, a hydrate or a solvate thereof according to the first aspect in the manufacture of a medicament for treating and/or preventing an infection by a parasite (including protozoan, helminth, etc.), Hepatitis B (HBV), Hepatitis C (HCV), influenza, a viral infectious disease caused by Rotavirus or Norovirus (e.g., viral enterogastritis caused by Rotavirus or Norovirus), or an infection caused by a bacterium such as *Clostridium difficile* or *Tubercle bacillus* (including drug-resistant *Tubercle bacillus*) or *Helicobacter pylori,* or in the manufacture of a medicament for inhibiting biofilm formation caused by a bacterium.

In the fifth aspect, the invention provides a method for treating and/or preventing a disease in a mammal in need thereof, comprising administering to the mammal in need thereof a therapeutically and/or prophylactically effective amount of the pharmaceutical composition according to the third aspect or the compound of Formula I or a pharmaceutically acceptable salt, hydrate or solvate thereof according to the first aspect, wherein the disease includes an infection by a parasite (including protozoan, helminth, etc.), Hepatitis B (HBV), Hepatitis C (HCV), influenza, a viral infectious disease caused by Rotavirus or Norovirus (e.g., viral enterogastritis caused by Rotavirus or Norovirus), or an infection caused by a bacterium such as *Clostridium difficile* or *Tubercle bacillus* (including drug-resistant *Tubercle bacillus*) or *Helicobacter pylori.*

In the sixth aspect, the invention provides a method for inhibiting biofilm formation caused by a bacterium in a mammal in need thereof, comprising administering to the mammal in need thereof a therapeutically and/or prophylactically effective amount of the pharmaceutical composition according to the third aspect or the compound of Formula I or a pharmaceutically acceptable salt, hydrate or solvate thereof according to the first aspect.

In the seventh aspect, the invention relates to at least one said compound of Formula I or a pharmaceutically acceptable salt, hydrate or solvate thereof, for use in the treatment and/or prevention of an infection by a parasite (including protozoan, helminth, etc.), Hepatitis B (HBV), Hepatitis C (HCV), influenza, a viral infectious disease caused by Rotavirus or Norovirus (e.g., viral enterogastritis caused by Rotavirus or Norovirus), or an infection caused by a bacterium such as *Clostridium difficile* or *Tubercle bacillus* (including drug-resistant *Tubercle bacillus*) or *Helicobacter pylori,* or for use in the inhibition of biofilm formation caused by a bacterium.

In the context, said parasite includes: *Giardia, Amoebae, Cryptosporidium, Cyclospora, Trichomonad, Encephalitozoon intestinalis, Isospora Blastocystis hominis, Balantidium coli, Ascaris lumbricoides, Enterocytozoon bieneusi,* Tapeworm (including *Taenia saginata, Hymenolepis nana*), *Diplacanthus nanus, Giardia Leishmania,* or *Fasciola hepatica,* etc.

In the context, said suitable base may be an organic base, or an inorganic base, such as sodium hydroxide, potassium hydroxide, calcium hydroxide, or meglumine.

In the context, said suitable acid may be an organic acid, or an inorganic acid, such as hydrochloric acid, sulphuric acid, acetic acid, or nitric acid.

The term "alkyl" used herein refers to a saturated, linear or branched monovalent hydrocarbyl, having 1-12 carbon atoms, preferably 1-6, 1-4 or 1-3 carbon atoms. Typical examples of "$C_{1-6}$alkyl" include, but are not limited to methyl, ethyl, n-propyl, isopropyl, n-butyl, isobutyl, teatbutyl, n-pentyl, tert-amyl, neo-pentyl, hexyl, etc.

The term "aryl" used herein refers to an unsaturated aromatic carbon ring having one single ring or two or more fused rings and 5-14 carbon atoms. Said aryl preferably has 5-10, 5-8 or 5-6 carbon atoms. Typical examples of "aryl" include, but are not limited to phenyl, naphthyl, anthryl, etc.

The term "amino" used herein refers to —$NH_2$.

The term "hydroxyl" used herein refers to —OH.

The term "nitro" used herein refers to —$NO_2$.

The term "cyano" used herein refers to —CN.

The term "alkoxy" used herein refers to —OR', wherein R' is the alkyl defined herein. Typical examples of "alkoxyl" include, but are not limited to methoxyl, ethoxyl, n-propoxy, isopropoxy, n-butoxy, tert-butoxy, sec-butoxy, etc.

The term "halogen" used herein refers to F, Cl, Br or I. The preferred halogen is F, Cl or Br.

When the name of a compound used herein is not consistent with the chemical formula, the chemical formula will prevail.

BENEFICIAL EFFECTS OF THE INVENTION

The invention provides tizoxanide phosphate or alkane sulfonate compounds of formula I, which can be converted into the form of tizoxanide in vivo so as to exert an action against protozoans, helminths, viruses or bacteria. In addition, the compounds of Formula I can significantly improve the bioavailability and the blood concentration calculated as tizoxanide, retain the effective blood concentration for a longer time, and make the blood concentration curve more stable.

SPECIFIC MODES FOR CARRYING OUT THE INVENTION

Figure 1:
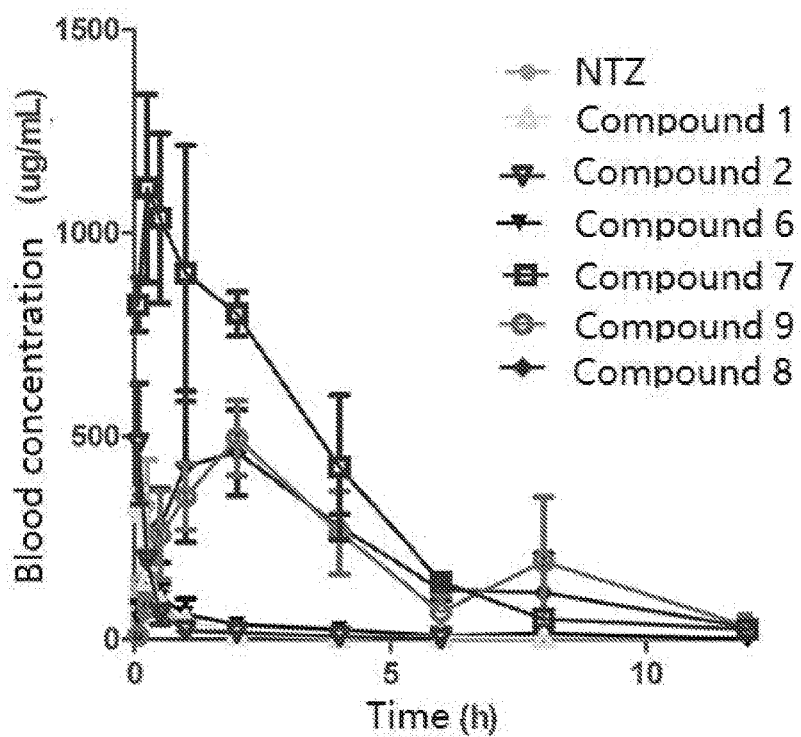
FIG. 1: The blood concentration-time curves of tizoxanide (TIZ) in blood after oral administration of nitazoxanide (NTZ), Compound 1, 2, 6, 7, 8, and 9 in mice, respectively.

The embodiments of the invention are described in detail by combining the following examples. However, a person skilled in the art will understand that the following examples are only provided for the purpose of describing the invention, and shall not be regarded as defining the scope of the invention. When the particular conditions are not indicated in Examples, the invention is carried out according to the conventional conditions or the conditions suggested by the manufacturer. The reagents or apparatuses, the manufacturers of which are not indicated, are the conventional products that are commercially available.

Example 1

Preparation of dibenzyl 2-(5-nitrothiazol-2-yl-carbamoyl)phenyl phosphate (Compound 1)

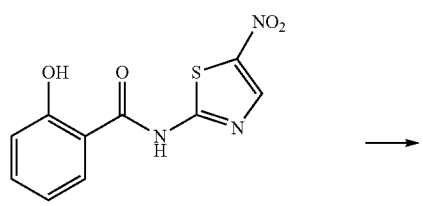

Molecular Weight 265.25
TIZ

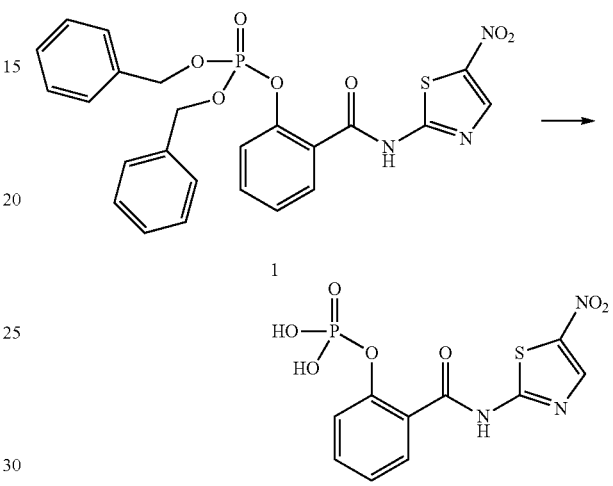

1

To a solution of tizoxanide (3.12 g, 12 mmol) in acetonitrile (150 mL), under the protection of N₂, at 0° C., carbon tetrachloride (9.61 g, 62.4 mmol), diisopropylethylamine (3.4 g, 26.4 mmol), 4-(N,N-dimethylamino)pyridine (180 mg, 1.32 mmol), and dibenzyl phosphite (90%) (6.0 g, 20.6 mmol) are added sequentially, stirred at the same temperature for 3 h. The reaction solution was poured into 450 mL ice water, and washed with 150 mL dichloromethane for three times. The organic phases were combined, and washed with 2 mol/L hydrochloric acid, saturated NaHCO₃ aqueous solution, and saturated saline solution sequentially, then dried with anhydrous sodium sulfate. The solvent was removed by distillation under reduced pressure, and the residue was solidified in ether, to obtain the title compound as white powder, with a yield of 79.3%, melting point (mp): 122-123° C., ¹H-NMR(DMSO-d6, 400 MHz), δppm, 13.64 (1H, brs), 8.66(1H,s), 7.75(1H,d,J=7.6 Hz), 7.64(1H,td, J=8.0 Hz, 2.0 Hz), 7.38-7.43(2H,m), 7.28-7.34(10H,m), 5.12(4H, m). ESI-MS(+Q), 526(MH⁺), 548(MNa⁺).

Example 2

Preparation of 2-(5-nitrothiazol-2-yl-carbamoyl)phenyl dihydrogen phosphate (Compound 2)

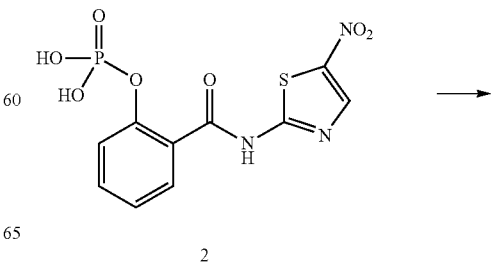

At 0° C., under the protection of N₂, to a suspension of Compound 1 (5.0 g, 9.52 mmoL) in anhydrous acetonitrile (90 mL), bromotrimethylsilane (3.70 mL, 28.33 mmoL) was added, reacted at 0° C. for 3 h, then anhydrous ethanol (2.7 mL, 47 mmoL) was added, and then stirred for 4 h. The resultant mixture was subjected to suction filtration, washed with ethyl acetate, and air-dried to obtain a product as yellow solid powder, 2.63 g, with a yield of 80%; mp: 224-226° C., ¹H-NMR (DMSO-d6, 400 MHZ) δ: 8.69(1H,s), 7.67(1H, m), 7.62(1H,m), 7.42(1H,m), 7.32(1H,m). ESI-MS(-Q): 344 [M–H]⁺; 264 [TIZ–H]⁺.

Example 3

Preparation of 2-(5-nitrothiazol-2-yl-carbamoyl)phenyl hydrogen phosphate monosodium salt (Compound 3)

-continued

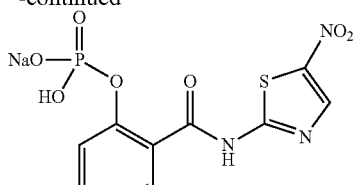

3
Molecular Weight: 367.21

Compound 2 (354.23 mg, 1 mmol) prepared in Example 2 was suspended in methanol 20 mL, and 2 mol/L NaOH aqueous solution (0.5 mL, 1 mmol) was added, stirred at room temperature for 20 min, the sample was dissolved completely. The resultant solution was concentrated up to dryness under reduced pressure, and dried in vacuum at 50° C. to obtain the title compound 367 mg, with a yield of 100%, mp: 260-263° C., IR(KBr)cm-1:3448, 1664, 1576, 1478, 1354, 1318, 1279, 1229, 923.

Example 4

Preparation of 2-(5-nitrothiazol-2-yl-carbamoyl)phenyl phosphate disodium salt (Compound 4)

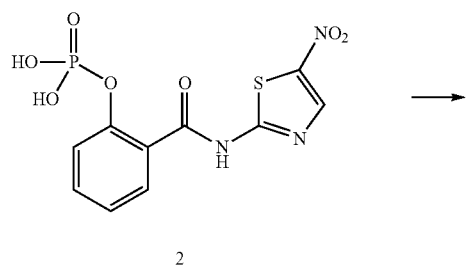

2

↓

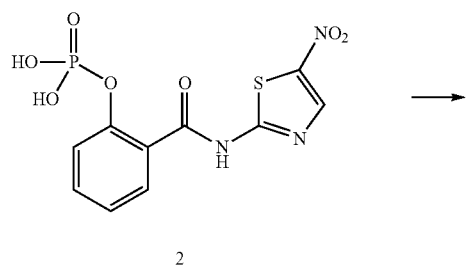

4

Compound 2 (354.23 mg, 1 mmol) prepared in Example 2 was suspended in methanol 20 mL, and 2 mol/L NaOH aqueous solution (1 mL, 2 mmol) was added, stirred at room temperature for 20 min, the sample was dissolved completely. The resultant solution was concentrated up to dryness under reduced pressure, and dried in vacuum at 50° C. to obtain the title compound 398 mg, with a yield of :100%, mp: 192-194° C., IR(KBr)cm-1:3424, 1656, 1477, 1356, 1309, 1215, 1096, 982, 907.

Example 5

Preparation of 2-(5-nitrothiazol-2-yl-carbamoyl)phenyl phosphate calcium salt (Compound 5)

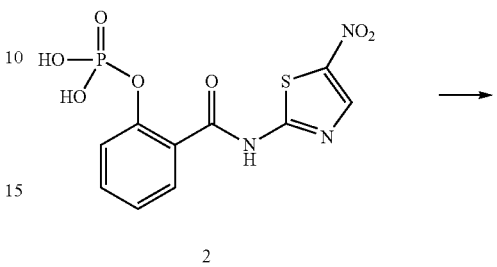

2

↓

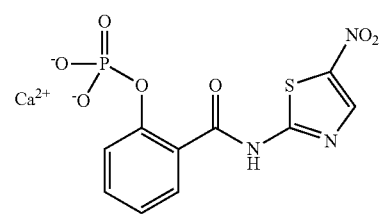

5

Compound 2 (354.23 mg, 1 mmol) prepared in Example 2 was suspended in methanol 20 mL, and 2 mol/L calcium acetate aqueous solution (0.5 mL, 1 mmol) was added. The resultant mixture was stirred at room temperature for 20 min, then concentrated, and then dried at 50° C. in vacuum, to obtain the title compound 313 mg, with a yield of 80%, mp: 238-241° C., IR(KBr)cm-1:3558, 3268, 1662, 1601, 1524, 1468,1365,1316, 1.220, 1170,1106,996,912,738.

Example 6

Preparation of 2-(5-nitrothiazol-2-yl-carbamoyl)phenyl methanesulfonate (Compound 6)

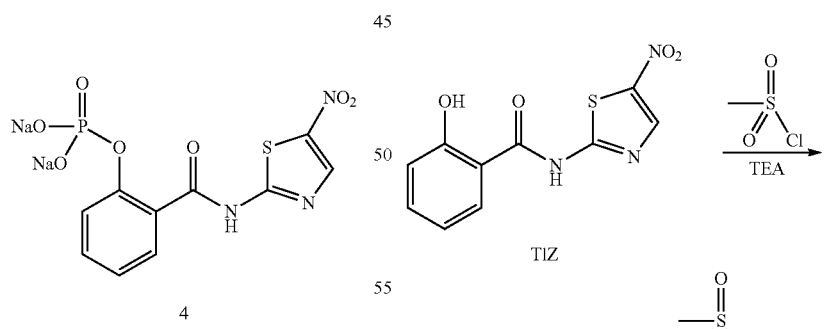

TIZ

↓

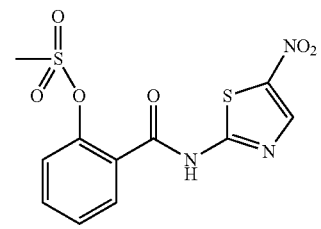

6

To a solution of tizoxanide (0.50 g, 1.89 mmol) in anhydrous N,N-dimethylformamide (20 mL), triethylamine (0.38 g, 3.78 mmol) was added. The temperature was reduced to 0° C., and methanesulfonyl chloride (0.24 g, 2.07 mmol) was added. The temperature was gradually increased to room temperature, at which the reaction was carried out under stirring. When TLC detection showed that raw materials disappeared, the reaction solution was added into water, and extracted with ethyl acetate. The ethyl acetate phase was washed with water and saturated saline solution sequentially, and dried with anhydrous sodium sulphonate and concentrated, and then was purified by silica gel column chromatography, to obtain the product 0.51 g, with a yield of 86.58%, mp: 188-190° C., $^1$H-NMR (DMSO-d6, 400 Hz) δ ppm:13.68(1H, s), 8.71(1H,s), 7.83(1H, dd, J=1.82, 8.02 Hz), 7.77-7.72 (1H,m), 7.58-7.54 (2H,m), 3.37(1H,s) . ESI-MS (+Q), m/z:344.1[M+H]$^+$, 366.0[M+Na]$^+$.

Example 7

Preparation of 2-(5-nitrothiazol-2-yl-carbamoyl)phenyl ethanesulfonate (Compound 7)

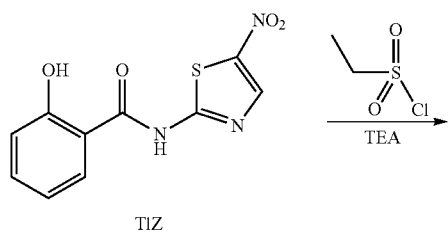

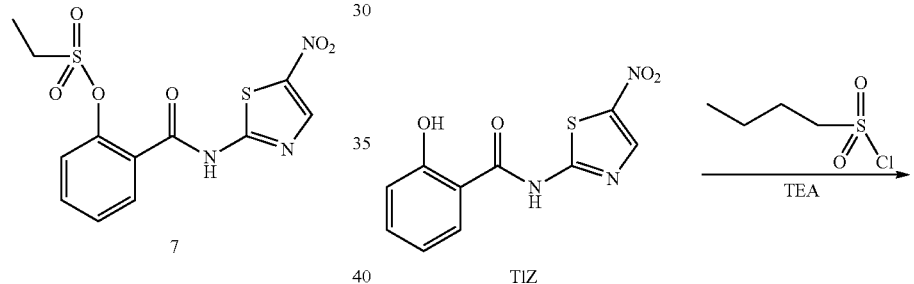

Except that ethanesulfonyl chloride was used in place of methanesulfonyl chloride to react with tizoxanide, the method of Example 6 was carried out to obtain the title compound, with a yield of 85.93%, mp: 178-180° C., $^1$H-NMR(DMSO-d6, 400 Hz) δppm: 13.69(s,1H), 8.71(s, 1H), 7.82 (dd, J=1.68, 7.56 Hz, 1H), 7.76-7.71(m, 1H), 7.57-7.51(m, 2H), 3.55(q, J=8.0 Hz, 2H), 1.32(t, J=8.0 Hz, 3H). ESI-MS m/z: 358.2[M+H]$^+$, 380.3[M+Na]$^+$.

Example 8

Preparation of 2-(5-nitrothiazol-2-yl-carbamoyl)phenyl 1-propanesulfonate (Compound 8)

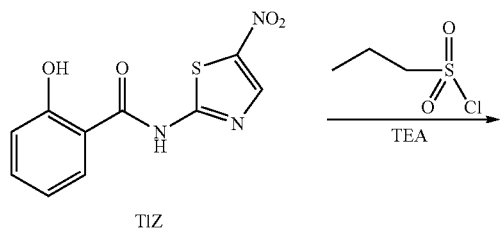

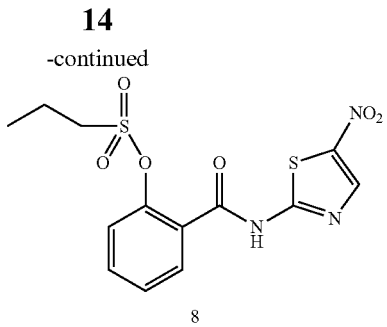

Except that 1-propanesulfonyl chloride was used in place of methanesulfonyl chloride to react with tizoxanide, the method of Example 6 was carried out to obtain the title compound, with a yield of 88.57%, mp: 144-146° C., 1H-NMR (DMSO-d6,400 Hz)δppm: 13.68(s,1H), 8.72(s, 1H), 7.83-7.71(m,2H), 7.57-7.51(m,2H), 3.52(t,J=8.0 Hz,2H), 1.82-1.76(m,2H), 0.96(t,J=6.0 Hz,3H). ESI-MS(+Q)m/z: 372.0[M+H]$^+$, 394.2[M+N]$^+$.

Example 9

Preparation of 2-(5-nitrothiazol-2-yl-carbamoyl)phenyl 1-butanesulfonate (Compound 9)

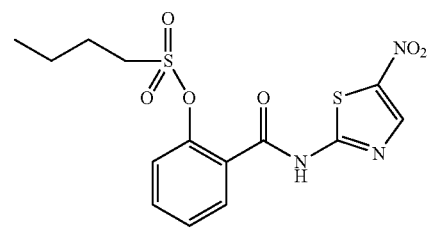

Except that 1-butanesulfonyl chloride was used in place of methanesulfonyl chloride to react with tizoxanide, the method of Example 6 was carried out to obtain the title compound, with a yield of 92.03%, mp: 142-144° C., 1H-NMR(CDCl3,400 Hz) δ ppm: 10.81(s,1H), 8.25(s,1H), 8.01(dd,J=1.82, 7.70 Hz, 1H), 7.72-7.55(m,1H), 7.53-7.50 (m,2H), 3.47(t,J=8.0,2H), 2.04-2.00(m,2H), 1.57-1.51(m, 2H), 0.97(t,J=8.0,3H). ESI-MS m/z: 386 [M+H]$^+$, 408 [M+Na]$^+$.

Example 10

Preparation of 2-(5-nitrothiazol-2-yl-carbamoyl)phenyl p-toluenesulfonate (Compound 9)

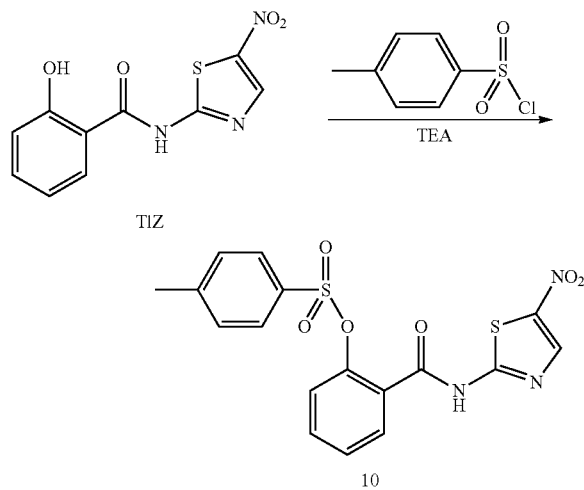

Except that p-toluenesulfonyl chloride was used in place of methanesulfonyl chloride to react with tizoxanide, the method of Example 6 was carried out to obtain the title compound, with a yield of 84.81%, mp: 236-238° C., 1H-NMR(DMSO-d6, 400 Hz)δppm:13.37(s, 1H), 8.71(s, 1H), 7.71-7.67(m, 2H), 7.53-7.50(m, 3H), 7.33-7.28(m, 3H), 2.29(s, 3H). ESI-MS m/z:420 [M+H]⁺, 442 [M+Na]⁺.

Example 11

Preparation of 2-(5-nitrothiazol-2-yl-carbamoyl)phenyl N-Boc-taurate (Compound 11)

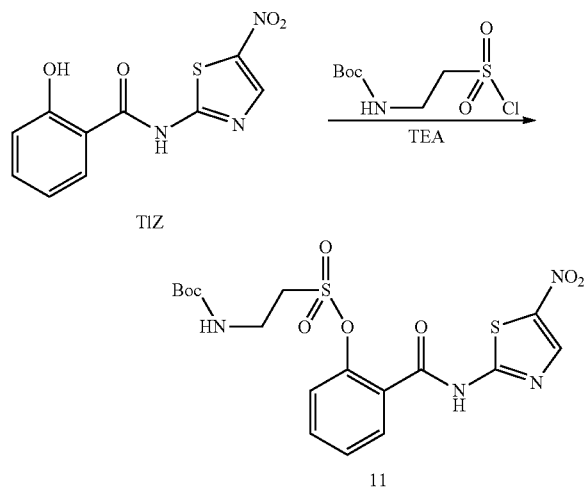

(1) Preparation of N-Boc-tauryl chloride solution: in a dried three-necked flask equipped with a thermometer and a drying pipe, freshly prepared N-Boc-taurine tetrabutylammonium (3.74 g, 8 mmol) was added, and dissolved with dichloromethane (28 mL), and then DMF 0.016 mL was added. The temperature of the resultant solution was reduced to 0° C., triphosgene (0.95 g, 3.2 mmol) was added, and the resultant mixed was gradually warmed to room temperature and reacted for 0.5 h.

(2) To a suspension of tizoxanide (1.59 g, 6 mmol) in 20 mL DMF, triethylamine (1.41 g, 14 mmol) was added, and the temperature was reduced to 0° C. The N-Boc-tauryl chloride solution prepared in the step (1) was added, and the resultant mixture was warmed to room temperature and reacted for 7 h. The reaction solution was poured into ice water, and the organic phase was separated. The water phase was washed with dichloromethane twice. The washings were combined with the organic phase, washed with dilute hydrochloric acid, washed with water, and washed with saturated NaCl solution, and dried with Na₂SO₄, and then concentrated, then Flash column chromatography (eluent is a mixture of ethyl acetate and petroleum ether at a volume ratio of 1:1) was carried out to obtain the target product, 1.6 g, with a yield of 56%. mp: 164-166° C., 1H-NMR(DMSO-d6,400 Hz) δppm: 13.70(s,1H), 8.71(s,1H), 7.84(m,1H), 7.73(m,1H), 7.56(m,2H), 7.08(t, J=5.6 Hz), 3.64(m,2H), 3.41(m,2H), 1.36(s,9H), ESI-MS m/z:473 [M+H]+.

Example 12

Preparation of 2-(5-nitrothiazol-2-yl-carbamoyl)phenyl taurate hydrochloride (Compound 12)

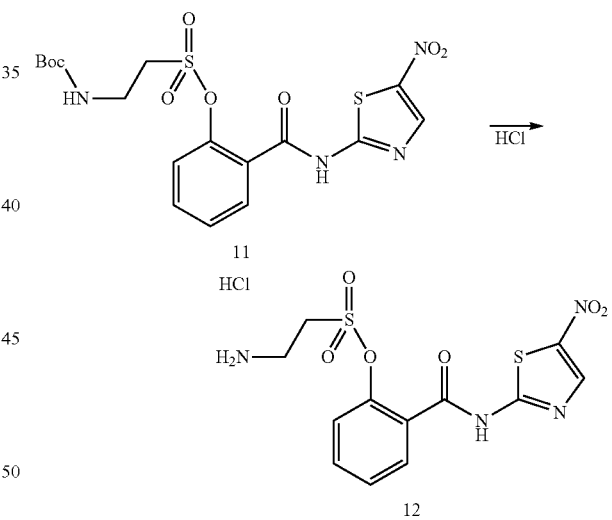

A solution of 1 mol/L HCl in ethyl acetate (10 mL, said solution of HCl in ethyl acetate refers to a solution formed by dissolving HCl gas in ethyl acetate) was cooled to 0° C., and 2-(5-nitrothiazol-2-yl-carbamoyl)phenyl N-Boc-taurate (Compound 11, 472 mg, 1 mmol) prepared in Example 11 was added. The resultant mixture was gradually warmed to room temperature and reacted for 4 h. The reaction solution was filtered under suction to obtain a solid. The solid was first dissolved in methanol, and then was recrystallized by adding isopropanol to obtain the product 380 mg, with a yield of 93%, mp: 168-470° C., ¹H-NMR (DMSO-d6, 400 Hz) δ ppm: 13.73(s,1H), 8.72(s,1H), 8.35(brs,3H), 7.87(d, J=7.6 Hz,1H), 7.75-7.79(m,1H), 7.58-7.65(m,2H), 3.96-4.00(m,2H), 3.32(m,2H). ESI-MS m/z:373 [M+H]⁺.

Example 13

Preparation of 2-(5-nitrothiazol-2-yl-carbamoyl)phenyl taurate (Compound 13)

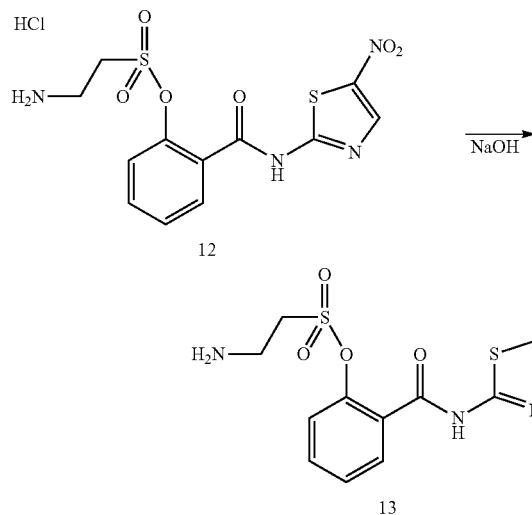

The 2-(5-nitrothiazol-2-yl-carbamoyl)phenyl taurate hydrochloride (Compound 12) prepared in Example 12 was dissolved in ethyl acetate, and equimolar NaOH aqueous solution was added, stirred sufficiently. The resultant mixture was washed with water, and the organic phase was dried with $Na_2SO_4$. After concentration, the title compound was obtained.

Example 14

Preparation of 2-(5-nitrothiazol-2-yl-carbamoyl)phenyl hydrogen phosphate monopotassium (Compound 14)

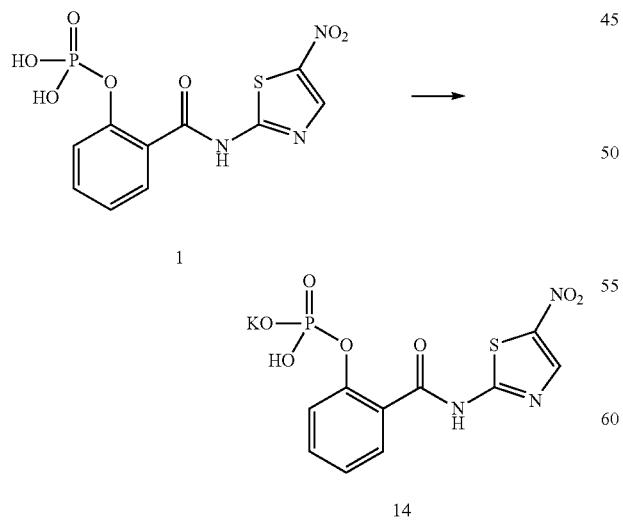

Compound 2 (354.23 mg, 1 mmol) prepared in Example 2 was suspended in methanol 20 mL, and 2 mol/L KOH aqueous solution (0.5 mL, 1 mmol) was added, stirred at room temperature for 20 min., the sample was dissolved completely. The resultant solution was concentrated up to dryness under reduced pressure, and dried in vacuum at 50° C. to obtain the title compound 383 mg, with a yield of 100%, mp: 252-264° C., IR(KBr)cm-1:3423, 3333, 1671, 1528, 1465,1358, 1313, 921.

Example 15

Preparation of 2-(5-nitrothiazol-2-yl-carbamoyl)phenyl phosphate dipotassium salt (Compound 15)

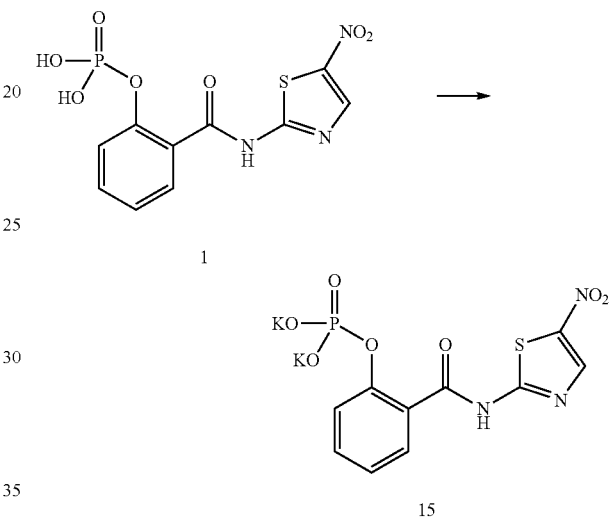

Compound 2 (354.23 mg, 1 mmol) prepared in Example 2 was suspended in methanol 20 mL, and 2 mol/L KOH aqueous solution (1 mL, 2 mmol) was added. stirred at room temperature for 20 min, the sample was dissolved completely. The resultant solution was concentrated up to dryness under reduced pressure, and dried in vacuum at 50° C. to obtain the title compound 422 mg, with a yield of 100%. mp: 192-194° C., IR(KBr)cm-1:3424, 1656, 1477, 1356, 1309, 1215, 1096, 982, 907.

Example 16

Preparation of 2-(5-nitrothiazol-2-yl-carbamoyl)phenyl hydrogen phosphate meglumine salt (Compound 16)

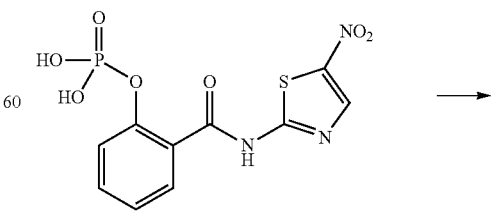

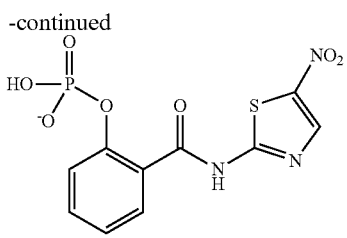

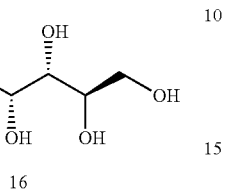

16

Compound 2 (354.23 mg, 1 mmol) prepared in Example 2 was suspended in methanol 20 mL, and a solution of meglumine (195.22 mg, 1 mmol) in methanol 10 ml, stirred at room temperature for 20 min, the resultant mixture was concentrated, and dried at 50° C. in vacuum to obtain the title compound 550 mg, as amorphous solid, with a yield of 100%.

Example 17

Preparation of dimethyl 2-(5-nitrothiazol-2-yl-carbamoyl)phenyl phosphate (Compound 17)

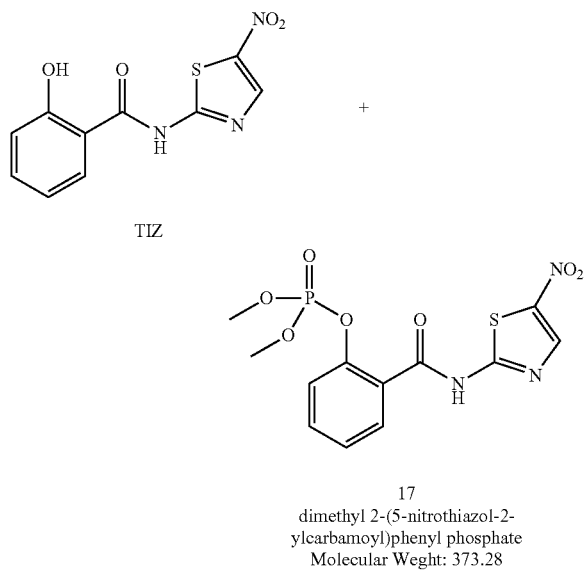

17
dimethyl 2-(5-nitrothiazol-2-ylcarbamoyl)phenyl phosphate
Molecular Weght: 373.28

To a solution of tizoxanide (3.12 g, 12 mmol) in acetonitrile (150 mL), under the protection of $N_2$, at 0° C., carbon tetrachloride (9.61 g, 62.4 mmol), diisopropylethylamine (3.4 g, 26.4 mmol), 4-(N,N-dimethylamino)pyridine (180 mg, 1.32 mmol), and dimethyl phosphite (90%) (2.52 g, 20.6 mmol) were added sequentially, stirred at the same temperature for 3 h, then the reaction solution was poured into 450 mL ice water, and washed with 150 mL dichloromethane for three times. The organic phases were combined, and then washed sequentially with 2 mol/L hydrochloric acid, saturated $NaHCO_3$ aqueous solution, and saturated saline solution, then dried with anhydrous sodium sulfate, the solvent was removed by distillation under reduced pressure, and the residue was solidified in ether to obtain the title compound 3.2 g, as white powder, with a yield of 72%, mp: 165-167° C., $^1$H NMR (400 MHz, CDCl3) δ 11.78-11.52 (m, 1H), 8.33 (s, 1H), 8.00 (d, J=8.1 Hz, 1H), 7.61 (td, J=8.1, 1.8 Hz, 1H), 7.45-7.35 (m, 2H), 3.96 (s, 3H), 3.93 (s, 3H). ESI-MS m/z:374 [M+H]$^+$, 396[M+Na]$^+$.

Example 18

Preparation of diethyl 2-(5-nitrothiazol-2-yl-carbamoyl)phenyl phosphate (Compound 18)

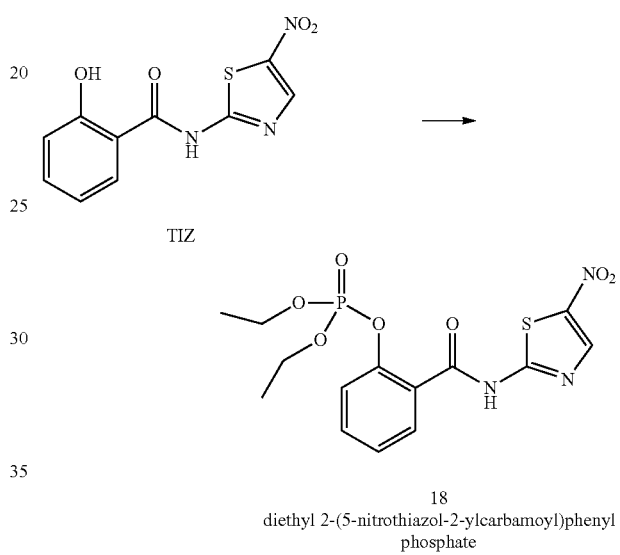

18
diethyl 2-(5-nitrothiazol-2-ylcarbamoyl)phenyl phosphate
Molecular Weight: 401.33

To a solution of tizoxanide (3.12 g, 12 mmol) in acetonitrile (150 mL), under the protection of $N_2$, at 0° C., carbon tetrachloride (9.61 g, 62.4 mmol), diisopropylethylamine (3.4 g, 26.4 mmol), 4-(N,N-dimethylamino)pyridine (180 mg, 1.32 mmol), and diethyl phosphite (98%) (2.90 g, 20.6 mmol) were added sequentially, followed by stirring at the same temperature for 3 h. The reaction solution was poured into 450 mL ice water, and washed with 150 mL dichloromethane for three times. The organic phases were combined, washed sequentially with 2 mol/L hydrochloric acid, saturated $NaHCO_3$ aqueous solution, and saturated saline solution, and dried with anhydrous sodium sulfate, the solvent was removed by distillation under reduced pressure, and the residue was solidified in ether to obtain the title compound 3.6 g, as white powder, with a yield of 75%, mp: 138-138° C., $^1$H NMR (400 MHz, CDCl3) δ 11.83-11.68 (m, 1H), 8.37 (s, 1H), 8.03 (d, J=7.6 Hz, 1H), 7.60 (t, J=7.6 Hz, 1H), 7.46-7.34 (m, 2H), 4.31 (dd, J=15.0, 7.2 Hz, 4H), 1.38 (t, J=7.2 Hz, 6H). ESI-MS m/z:402 [M+H]$^+$, 424[M+Na]$^+$.

Example 19

Pharmacokinetic Evaluation and Result of Oral Administration of Drug in Mice

Sample preparation: 32.57 μmol of a test compound was dissolved in 100 μL dimethyl sulfoxide (DMSO), with the addition of 10 mL 0.5% Carboxyl Methyl Cellulose Sodium (CMC-Na) solution, to prepare a sample at 3.257 μmol/mL.

The test compounds refer to the compounds prepared in Examples of the invention and the positive control compound nitazoxanide. The experiment was carried out in two batches, wherein the first batch of test compounds were Compound 1, 2, 6, 7, 8, 9 and the positive control compound nitazoxanide; and the second batch of test compounds were Compound 3, 4, 5, 12, 14, 17, 18 and positive control compound nitazoxanide.

Experimental method: ICR mice (SPS grade, male, 25±2 mg), purchased from Beijing Vital River Laboratory Animal Technology Co., Ltd., were grouped randomly depending on body weight, 3 mice for each group. Nitazoxanide and a test compound were intragastrically administered separately to each mouse at a dose of 10 mL/kg (i.e., 32.57 μmol/kg of corresponding drug to each mouse), wherein nitazoxanide was used as positive control, and 0.1 ml blood was taken from veins of Fundus Oculi at 0.08, 0.25, 0.5, 1, 2, 4, 6, 8 and 12 h after administration, placed in a Heparin Sodium-containing centrifuge tube, and centrifuged for 20 min (at a relative centrifugal force (RCF) of 3000 g). The plasma was taken and stored in a −20° C. refrigerator for further detection.

Figure 2:
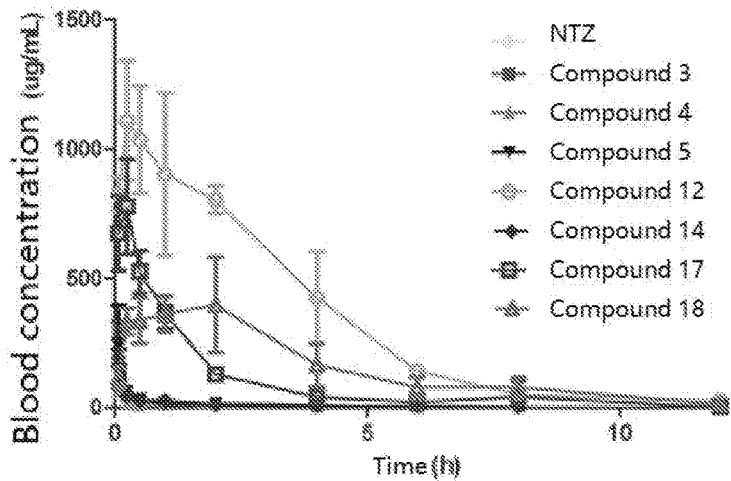
FIG. 2: the blood concentration-time curves of tizoxanide (TIZ) in blood after oral administration of nitazoxanide (NTZ), Compound 3, 4, 5, 12, 14, 17 and 18 in mice, respectively.

During the detection, 50 μL plasma was taken, with the addition of an internal standard solution (5000 ng/mL glipizide aqueous solution, 10 μL), and the addition of acetonitrile (200 μL), and then mixed well. The mixture was vortexed for 3 min, and centrifuged for 10 min (at a relative centrifugal force (RCF) of 8500 g). The supernatant (50 μL) was well mixed with water (50 μL), and 10 μL was drawn for LC/MS/MS analysis, so as to detect the blood concentration of tizoxanide. The results are shown in Table 1, Table 2, Table 3, Table 4, FIG. 1, and FIG. 2.

TABLE 1

Blood concentrations (Mean ± SD, n = 3) of tizoxanide (TIZ) after oral administration of the compound nitazoxanide (NTZ) and Compound 1, 2, 6, 7, 8, 9 in mice, respectively

| time (h) | nitazoxanide (NTZ) | Compound 1 | Compound 2 | Compound 6 | Compound 7 | Compound 8 | Compound 9 |
|---|---|---|---|---|---|---|---|
| 0.08 | 127.23 ± 22.46 | 329.85 ± 37.88 | 480.66 ± 149.04 | 48.59 ± 43.66 | 619.23 ± 131.29 | 19.43 ± 7.97 | 9.64 ± 4.60 |
| 0.25 | 329.39 ± 111.17 | 148.92 ± 24.08 | 195.50 ± 19.09 | 67.85 ± 6.50 | 360.27 ± 108.54 | 118.19 ± 21.09 | 83.17 ± 24.73 |
| 0.5 | 94.65 ± 24.48 | 92.03 ± 11.37 | 60.77 ± 24.24 | 103.21 ± 32.66 | 149.92 ± 2.98 | 279.55 ± 91.07 | 256.43 ± 108.32 |
| 1 | 19.69 ± 5.62 | 48.61 ± 8.32 | 22.30 ± 0.75 | 62.11 ± 37.77 | 81.50 ± 0.62 | 425.24 ± 185.79 | 350.02 ± 81.51 |
| 2 | 13.91 ± 3.60 | 13.39 ± 2.27 | 17.66 ± 17.49 | 36.89 ± 9.46 | 13.63 ± 4.06 | 458.74 ± 105.51 | 495.02 ± 93.24 |
| 4 | 8.22 ± 5.08 | 4.18 ± 1.51 | 6.83 ± 6.01 | 23.95 ± 15.44 | 4.39 ± 1.92 | 276.56 ± 30.93 | 261.54 ± 101.72 |
| 6 | 3.46 ± 1.66 | 6.14 ± 4.10 | 2.30 ± 1.98 | 8.79 ± 4.53 | 0.38* | 121.68 ± 24.75 | 67.19 ± 39.27 |
| 8 | 0.61 ± 0.12 | 2.90 ± 1.04 | ND | 15.14 ± 16.34 | ND | 115.25 ± 97.00 | 190.64 ± 159.27 |
| 12 | 4.90 ± 6.45 | 0.51 ± 0.04 | 0.24* | 0.20* | 160.27 ± 108.54 | 30.30 ± 19.55 | 31.88 ± 26.74 |

Note:
ND: lower than limit of quantitation;
*a group of measured values, no SD value

TABLE 2

Blood concentrations (Mean ± SD, n = 3) of tizoxanide (TIZ) after oral administration of the compound nitazoxanide (NTZ) and Compound 3, 5, 12, 14, 17, 18 in mice, respectively

| time (h) | nitazoxanide (NTZ) | Compound 3 | Compound 5 | Compound 12 | Compound 14 | Compound 17 | Compound 18 |
|---|---|---|---|---|---|---|---|
| 0.08 | 86.46 ± 40.97 | 297.33 ± 35.74 | 243.54 ± 150.44 | 822.63 ± 66.11 | 194.90 ± 28.73 | 673.15 ± 144.19 | 114.79 ± 40.96 |
| 0.25 | 66.67 ± 39.16 | 45.68 ± 12.91 | 62.78 ± 18.56 | 1108.79 ± 231.35 | 45.812 ± 12.07 | 775.87 ± 184.95 | 333.65 ± 48.75 |
| 0.5 | 12.28 ± 5.86 | 35.49 ± 14.89 | 30.27 ± 17.02 | 1035.27 ± 208.56 | 24.38 ± 3.82 | 523.92 ± 81.61 | 335.98 ± 88.56 |
| 1 | 11.90 ± 1.00 | 19.83 ± 8.06 | 13.28 ± 4.02 | 900.50 ± 315.32 | 29.36 ± 3.83 | 367.09 ± 61.76 | 359.85 ± 67.39 |
| 2 | 4.65 ± 2.62 | 18.75 ± 4.75 | 10.14 ± 5.43 | 800.59 ± 54.04 | 8.64 ± 4.27 | 127.95 ± 12.91 | 395.59 ± 183.65 |
| 4 | 7.57 ± 2.32 | 9.04 ± 5.39 | 7.50 ± 2.43 | 422.98 ± 178.48 | 4.71 ± 2.33 | 40.80 ± 2.68 | 163.62 ± 82.72 |
| 6 | 4.43 ± 2.15 | 1.63 * | 2.66 ± 1.09 | 141.20 ± 4.14 | 6.65 ± 5.84 | 21.21 ± 23.33 | 78.99 ± 37.79 |
| 8 | 1.54 ± 0.55 | 2.16 ± 1.30 | 1.49 ± 0.28 | 50.31 ± 8.74 | 2.06 ± 1.00 | 4.99 ± 61.83 | 78.66 ± 36.77 |
| 12 | ND | | | 25.06 ± 1.72 | | 1.05 | 12.71 ± 13.04 |

TABLE 3

Pharmacokinetic parameters (Mean ± SD, n = 3) calculated as tizoxanide (TIZ), after oral administration of nitazoxanide (NTZ) and Compound 1, 2, 6, 7, 8, 9 in mice

| Parameters | Unit | nitazoxanide (NTZ) | Compound 1 | Compound 2 | Compound 6 | Compound 7 | Compound 8 | Compound 9 |
|---|---|---|---|---|---|---|---|---|
| $T_{max}$ | h | 0.25 ± 0.00 | 0.08 ± 0.00 | 0.08 ± 0.00 | 0.50 ± 0.00 | 0.80 ± 0.00 | 1.67 ± 0.58 | 2.00 ± 0.00 |

TABLE 3-continued

Pharmacokinetic parameters (Mean ± SD, n = 3) calculated as tizoxanide (TIZ), after oral administration of nitazoxanide (NTZ) and Compound 1, 2, 6, 7, 8, 9 in mice

| Parameters | Unit | nitazoxanide (NTZ) | Compound 1 | Compound 2 | Compound 6 | Compound 7 | Compound 8 | Compound 9 |
|---|---|---|---|---|---|---|---|---|
| $C_{max}$ | ng/mL | 329.4 ± 111.2 | 329.8 ± 37.9 | 480.7 ± 149.0 | 103.2 ± 32.7 | 619.2 ± 131.3 | 474.8 ± 128.1 | 495.0 ± 93.2 |
| Ke | 1/h | 0.41 ± 0.23 | 0.37 ± 0.11 | 0.72 ± 0.26 | 0.37 ± 0.20 | 0.62 ± 0.01 | 0.32 ± 0.05 | 0.33 ± 0.19 |
| $t_{1/2}$ | h | 2.02 ± 0.92 | 1.95 ± 0.59 | 1.09 ± 0.51 | 2.22 ± 1.23 | 1.22 ± 0.02 | 2.23 ± 0.36 | 2.54 ± 1.18 |
| $AUC_{0-t}$ | h*ng/mL | 185.8 ± 18.3 | 193.9 ± 14.7 | 183.1 ± 6.5 | 245.3 ± 84.1 | 330.2 ± 39.0 | 2158.4 ± 759.6 | 2413.0 ± 631.9 |
| $AUC_{0-\infty}$ | h*ng/mL | 198.5 ± 28.5 | 195.3 ± 15.1 | 187.7 ± 2.5 | 305.1 ± 168.0 | 345.1 ± 33.0 | 2313.5 ± 640.4 | 2559.1 ± 701.9 |
| $MRT_{0-t}$ | h | 1.46 ± 0.81 | 1.52 ± 0.17 | 0.90 ± 0.08 | 2.53 ± 0.24 | 0.73 ± 0.03 | 3.29 ± 0.57 | 4.05 ± 0.68 |
| $MRT_{0-\infty}$ | h | 2.15 ± 1.66 | 1.62 ± 0.15 | 1.08 ± 0.18 | 3.91 ± 2.16 | 0.87 ± 0.20 | 3.90 ± 0.48 | 4.73 ± 1.10 |
| $F_{(相对相对)}$ | % | 100 | 104.35 ± 7.93 | 98.54 ± 3.49 | 132.04 ± 45.27 | 174.24 ± 21.01 | 1161.56 ± 408.79 | 1298.60 ± 340.06 |

TABLE 4

Pharmacokinetic parameters (Mean ± SD, n = 3) calculated as tizoxanide (TIZ), after oral administration of nitazoxanide (NTZ) and Compound 3, 5, 12, 14, 17, 18 in mice

| Parameters | Unit | nitazoxanide (NTZ) | Compound 3 | Compound 5 | Compound 12 | Compound 14 | Compound 17 | Compound 18 |
|---|---|---|---|---|---|---|---|---|
| $T_{max}$ | h | 0.14 ± 0.10 | 0.08 ± 0.00 | 0.08 ± 0.00 | 0.33 ± 0.14 | 0.08 ± 0.00 | 0.25 ± 0.00 | 1.67 ± 0.58 |
| $C_{max}$ | ng/mL | 101.1 ± 36.7 | 297.3 ± 35.7 | 243.5 ± 150.4 | 1214.5 ± 53.3 | 194.9 ± 28.7 | 775.9 ± 185.0 | 460.5 ± 74.8 |
| Ke | 1/h | 0.34 ± 0.07 | 0.52 ± 0.22 | 0.44 ± 0.07 | 0.36 ± 0.00 | 0.51 ± 0.27 | 0.50 ± 0.08 | 0.37 ± 0.24 |
| $t_{1/2}$ | h | 2.07 ± 0.39 | 1.49 ± 0.52 | 1.60 ± 0.27 | 1.92 ± 0.01 | 1.60 ± 0.66 | 1.41 ± 0.23 | 2.47 ± 1.46 |
| $AUC_{0-t}$ | h*ng/mL | 69.2 ± 3.7 | 122.6 ± 17.1 | 99.1 ± 37.5 | 3929.6 ± 478.4 | 97.0 ± 17.2 | 1079.5 ± 70.6 | 1820.3 ± 392.3 |
| $AUC_{0-\infty}$ | h*ng/mL | 76.0 ± 7.9 | 127.6 ± 19.3 | 102.8 ± 37.1 | 3998.8 ± 481.9 | 101.8 ± 17.9 | 1176.6 ± 220.7 | 1883.3 ± 382.2 |
| $MRT_{0-t}$ | h | 2.10 ± 0.42 | 1.37 ± 0.33 | 1.42 ± 0.26 | 2.60 ± 0.15 | 1.53 ± 0.64 | 1.61 ± 0.24 | 3.34 ± 0.42 |
| $MRT_{0-\infty}$ | h | 2.79 ± 0.58 | 1.66 ± 0.44 | 1.78 ± 0.38 | 2.81 ± 0.16 | 1.90 ± 0.74 | 2.21 ± 1.07 | 3.81 ± 0.61 |
| $F_{(相对相对)}$ | % | — | 148.3 ± 20.7 | 114.8 ± 43.5 | 3956.7 ± 476.8 | 112.4 ± 19.9 | 1284.5 ± 84.0 | 2014.6 ± 434.1 |

The pharmacokinetic screening results after oral administration in mice show (see Table 1, Table 2, Table 3, Table 4, FIG. 1, and FIG. 2):

(1) Like nitazoxanide (NTZ), Compound 1, 2, 6, 7, 8, 9 and Compound 3, 4, 5, 12, 14, 17, 18 could be converted to the active form tizoxanide in vivo after oral administration in mice, and the conversion was relatively complete.

(2) After oral administration in mice, nitazoxanide-substituted phosphate compound—dibenzyl 2-(5-nitrothiazol-2-yl-carbamoyl)phenyl phosphate (Compound 1) had a shorter time to peak (Tmax) of tizoxanide in blood than that of the positive control agent nitazoxanide, had a Cmax similar to that of nitazoxanide, had an Area Under concentration-time Curve (AUC) slightly higher than that of nitazoxanide, and had a bioavailability (F) (calculated as tizoxanide) 1.04-fold higher than that of nitazoxanide. As to the other two nitazoxanide-substituted phosphate compounds—dimethyl 2-(5-nitrothiazol-2-yl-carbamoyl)phenyl phosphate (Compound 17) and diethyl 2-(5-nitrothiazol-2-yl-carbamoyl)phenyl phosphate (Compound 18), after oral administration in mice, they had a longer Tmax of tizoxanide in blood than that of the positive control agent nitazoxanide, had a Cmax and AUC obviously higher than that of nitazoxanide, and had a bioavailability (F) (calculated as tizoxanide) that was 12.8-fold and 20.1-fold of that of nitazoxanide.

(3) After oral administration, nitazoxanide dihydrogen phosphate (2-(5-nitrothiazol-2-yl-carbamoyl)phenyl dihydrogen phosphate, Compound 2), and salts thereof—including monosodium salt (Compound 3), disodium salt (Compound 4), calcium salt (Compound 5), and monopotassium (Compound 14), had a shorter time to peak (Tmax) of tizoxanide in blood than that of the positive agent nitazoxanide, had a higher Cmax than nitazoxanide, and had a bioavailability (F) (calculated as tizoxanide) similar to that of nitazoxanide.

(4) After oral administration in mice, tizoxanide alkane sulfonate compounds, including methanesulfonate (Compound 6), ethanesulfonate (Compound 7), tizoxanide propanesulfonate (Compound 8), tizoxanide butanesulfonate (Compound 9) and taurate hydrochloride (Compound 12), had a delayed time to peak (Tmax) of tizoxanide in blood compared to the positive agent nitazoxanide, had a significantly increased Cmax value compared to the positive compound nitazoxanide (except for Compound 6), and had a Mean Retention Time ($MRT_{0-\infty}$) of tizoxanide an vivo and an Area Under concentration-time Curve (AUC) much higher than that of nitazoxanide, and had a bioavailability (F) (calculated as tizoxanide) that was 1.32-fold, 1.74-fold, 11.6-fold, 13.0-fold and 39.6-fold of that of nitazoxanide, and were superior to nitazoxanide in some aspects.

Example 20

Pharmacokinetic Evaluation of Oral Administration and Intravenous Injection of Nitazoxanide and Compound 3 in Rats 9 SD rats (SPF grade, male, 200±10 g), provided by Laboratory Animal Center of the Academy of Military Medical Sciences, were grouped randomly, 3 mice for each group.

(1) Intravenous injection group of Compound 3: a dose of 5 mg/kg (equivalent to a dose of 13.67 μmol/kg tizoxanide); administration volume: 0.2 mL/200 g rat (preparation of a test solution: 15.00 mg Compound 3 prepared in Example 3 was weighed accurately and dissolved by adding 100 μL DMSO, and then sterile water was added to prepare a clear solution at 5 mg/mL), after intravenous injection of Compound 3 to the tail of rat, blood was taken at 0.03, 0.08, 0.25, 0.5, 1, 2, 4, 6, 8, 12, and 24 h after administration. The plasma was separated and stored in a −20° C. refrigerator for further detection.

(2) Oral administration group of Compound 3, a dose of 15 mg/kg (equivalent to a dose of 41 μmol/kg tizoxanide); administration volume: 2 mL/200 g rat (to the solution of Compound 3 (5 mg/mL) prepared above, sterile water was added to prepare a clear solution at 1.5 mg/mL); after oral administration of Compound 3 (a dose of 15 mg/kg) in rats, blood was taken at 0.08, 0.25, 0.5, 1, 2, 4, 6, 8, 12 and 24 h after administration. The plasma was separated and stored in a −20° C. refrigerator for further detection.

(3) Oral administration group of nitazoxanide: a dose of 12.5 mg/kg (equivalent to a dose of 41 μmol/kg tizoxanide); administration volume: 2 mL/200 g rat (preparation of a test solution: 10.96 mg nitazoxanide was weighed accurately and dissolved by adding 600 μL DMSO, and 8.768 mL sterile water was added to prepare a clear solution at 1.25 mg/mL); after oral administration of nitazoxanide at 12.5 mg/kg in rats, blood was taken before administration and at 0.08, 0.25, 0.5, 1, 2, 4, 6, 8, 12 and 24 h after administration. The plasma was separated and stored in a −20° C. refrigerator for further detection.

Treatment of plasma sample: 100 μL plasma was taken, 300 μL acetonitrile solution containing internal standard (500 nmol/L a solution of tolbutamide in acetonitrile) was added, and then mixed well. The mixture was vortexed for 1 min, and centrifuged at 4° C. for 10 min (at a relative centrifugal force (RCF) of 14000 g). The supernatant was taken, and 20 μL was drawn for LC/MS/MS analysis, so as to detect the blood concentration of tizoxanide and the prototype drug. The results are shown in Table 5 and Table 6.

TABLE 5

Blood concentration after oral administration or intravenous injection of Compound 3 and oral administration of nitazoxanide

| Time (h) | Intravenous injection of Compound 3 (5 mg/kg) plasma concentration of Compound 3 (ng/mL) Mean ± SD | Intravenous injection of Compound 3 (5 mg/kg) plasma concentration of tizoxanide (ng/mL) Mean ± SD | Oral administration of Compound 3 (15 mg/kg) plasma concentration of Compound 3 (ng/mL) Mean ± SD | Oral administration of Compound 3 (15 mg/kg) plasma concentration of tizoxanide (ng/mL) Mean ± SD | Oral administration of nitazoxanide (15 mg/kg) plasma concentration of tizoxanide (ng/mL) Mean ± SD |
|---|---|---|---|---|---|
| 0.03 | 26739.2 ± 6592.9 | 23315.3 ± 12019.0 | 55.3 ± 2.1 | 3053.5 ± 1860.6 | 677.3 ± 541.5 |
| 0.08 | 13255.6 ± 1386.3 | 18111.1 ± 8851.7 | 99.1 ± 22.1 | 2714.4 ± 1452.6 | 956.9 ± 408.1 |
| 0.25 | 3970.6 ± 1879.8 | 9856.5 ± 807.3 | 71.1 ± 7.3 | 1603.5 ± 891.8 | 989.0 ± 234.6 |
| 0.5 | 1730.3 ± 1249.3 | 5186.9 ± 763.4 | 33.0 ± 3.2 | 451.3 ± 52.4 | 743.7 ± 156.4 |
| 1 | 345.0 ± 316.5 | 1720.7 ± 899.3 | 24.4 ± 1.6 | 502.7 ± 513.2 | 235.4 ± 151.2 |
| 2 | 113.0 ± 83.4 | 343.8 ± 117.7 | — | 225.2 ± 257.2 | 60.1 ± 68.0 |
| 4 | 13.9 ± 1.9 | 31.2 ± 27.1 | — | 43.7 ± 22.6 | 37.9 ± 47.6 |
| 6 | — | 11.6 ± 10.4 | — | 153.7 ± 234.5 | 33.0 ± 28.0 |
| 12 | — | — | — | 12.8 ± 5.9 | 21.1 ± 16.9 |

TABLE 6

Pharmacokinetic parameters (Mean ± SD, n = 3) after oral administration or intravenous injection of Compound 3 and oral administration of nitazoxanide in rats

| Parameters | Unit | plasma concentration of tizoxanide | | | plasma concentration of Compound 3 | |
|---|---|---|---|---|---|---|
| | | intravenous injection of Compound 3 (5 mg/kg) | oral administration of Compound 3 (15 mg/kg) | oral administration of nitazoxanide (12.5 mg/kg) | intraveneus injection of Compound 3 (5 mg/kg) | oral administration of Compound 3 (15 mg/kg) |
| $C_{max}$ | μg/mL | 23.32 ± 12.02 | 3.05 ± 1.86 | 0.989 ± 0.23 | 26.74 ± 6.59 | 0.10 ± 0.02 |
| $T_{max}$ | h | — | 0.22 ± 0.24 | 0.42 ± 0.14 | — | 0.25 ± 0.00 |
| $t_{1/2z}$ | h | 0.50 ± 0.04 | 2.03 ± 0.37 | 3.16 ± 0.82 | 0.48 ± 0.28 | 1.67 ± 1.67 |
| $AUC_{(0-t)}$ | μg/L*h | 9199.0 ± 715.7 | 3378.7 ± 746.2 | 1967.1 ± 982.2 | 4916.5 ± 785.6 | 118.6 ± 50 |
| $AUC_{(0-\infty)}$ | μg/L*h | 9204.1 ± 712.7 | 3433.1 ± 718.9 | 1996.9 ± 974.1 | 4921.5 ± 785.9 | 153.8 ± 76.3 |
| $MRT_{(0-t)}$ | h | 0.47 ± 0.18 | 1.87 ± 0.65 | 2.01 ± 1.18 | 0.26 ± 0.15 | 1.22 ± 0.83 |
| $CL_{z/F}$ | L/h/kg | 0.55 ± 0.04 | 4.50 ± 0.94 | 7.34 ± 3.46 | 1.03 ± 0.17 | 112.79 ± 47.03 |
| $V_{z/F}$ | L/kg | 0.39 ± 0.05 | 13.53 ± 5.20 | 32.67 ± 16.81 | 0.69 ± 0.38 | 197.89 ± 118.02 |
| F | % | — | 12.2 | 7.2 | — | 2.4 |

The pharmacokinetic evaluation results after oral administration or intravenous injection of Compound 3 and oral administration of nitazoxanide in rats show (see Table 5, Table 6):

(1) Compound 3 has a solubility much better than nitazoxanide, with a solubility >1.0 mg/mL, can be prepared into a solution, and be administered orally or by intravenous or intramuscular injection, while nitazoxanide can only be administered orally in the form of suspension.

(2) Compound 3 can be quickly converted to its active form tizoxanide, no matter by oral administration or intravenous injection, and the concentration of prototype drug is smaller than that of tizoxanide.

(3) After oral administration of a solution of Compound 3 (1.5 mg/kg, equivalent to a dose of 41 μmol/kg tizoxanide) and a suspension of nitazoxanide (12.5 mg/kg, equivalent to a dose of 41 μmol/kg tizoxanide), the Compound 3 had a peak plasma concentration of 3.05±1.86 μg/mL for the active product tizoxanide, and an Area Under concentration-time Curve (AUC) of 3433.1±718.9 μg/L*h. Nitazoxanide had a peak plasma concentration of 0.989±0.23 μg/mL for the active product tizoxanide, and an Area Under concentration-time Curve (AUC) of 1996.9±974.1 μg/L*h. Compound 3 had a Cmax and a AUC value that were 3.1-fold and 1.7-fold of that of nitazoxanide, respectively. It can be determined by calculation that as compared to intravenous injection, Compound 3 had a bioavailability of 12.2% by oral administration in rats, while nitazoxanide had a bioavailability of 7.2%.

(4) After intravenous injection of a solution of Compound 3 (5 mg/kg), the Cmax value was 23.32 μg/ml, for tizoxanide in blood, and the Area Under concentration-time Curve [AUC(0-∞)] was 9204.1 μg/L*h, as calculated as tizoxanide. While after oral administration of nitazoxanide (12.5 mg/kg) in a 3-fold molar dose, the Cmax value for tizoxanide in blood was 0.989 μg/mL, and the Area Under concentration-time Curve [$AUC_{(0-\infty)}$] was 1996.9 μg/L*h. With the comparison of intravenous injection of Compound 3 with oral administration of nitazoxanide, the former was significantly superior with respect to the two parameters, i.e., Cmax and Area Under concentration-time Curve AUC (0-∞) as calculated as tizoxanide.

Conclusion: after oral administration of the tizoxanide alkane sulfonate compounds (such as Compound 6, 7, 8, 9 and 12) and the nitazoxanide-substituted phosphate compounds (such as Compound 17, 18) synthesized in the invention, the Cmax of tizoxanide in blood was significantly increased, and the bioavailability (F) calculated as tizoxanide was much higher than that of nitazoxanide. The tizoxanide dihydrogen phosphate compounds (such as Compound 2) and salts thereof (such as Compound 3, 4, 5, 14) synthesized in the invention, were similar to nitazoxanide in terms of bioavailability (F), but were much better than nitazoxanide in terms of solubility, and therefore can not only be administered orally, but also be injected intravenously. It is found by test that tizoxanide dihydrogen phosphate monosodium salt (Compound 3) administered intravenously was much better than nitazoxanide administered orally, with respect to the parameters such as blood concentration and bioavailability.

The invention claimed is:

1. A compound of Formula I, or a pharmaceutically acceptable salt, a hydrate or a solvate thereof,

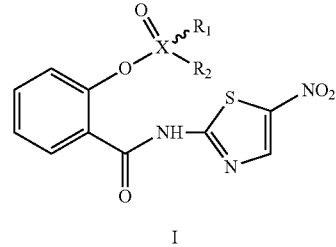

I wherein: X=P or S,
when X=P, " ︴ " represents a single bond, $R_1$ and $R_2$ each are independently hydroxyl or $C_{1-6}$alkoxy, said $C_{1-6}$alkoxy is optionally substituted by 1-2 substituents independently selected from the group consisting of: aryl, amino, hydroxyl, cyano, nitro, $C_{1-4}$alkyl and halogen, said aryl is optionally substituted by 1-2 substituents independently selected from the group consisting of: aryl, amino, hydroxyl, cyano, nitro, $C_{1-4}$alkyl and halogen; or
when X=S, " ︴ " represents a double bond, $R_1$ is O, $R_2$ is n-propyl, n-butyl, or aminoethyl, said n-propyl or n-butyl is optionally substituted by 1-2 substituents independently selected from the group consisting of: amino, hydroxyl, cyano, nitro, and halogen.

2. The compound, or a pharmaceutically acceptable salt, a hydrate or a solvate thereof according to claim 1, wherein, X=P, "⌇" represents a single bond, $R_1$ and $R_2$ each are independently hydroxyl or $C_{1-4}$alkoxy, said $C_{1-4}$alkoxy is optionally substituted by 1-2 substituents independently selected from the group consisting of: phenyl, amino, hydroxyl, cyano, nitro, $C_{1-4}$alkyl and halogen, said phenyl is optionally substituted by 1-2 substituents independently selected from the group consisting of: amino, hydroxyl, cyano, nitro, $C_{1-4}$alkyl and halogen.

3. The compound, or a pharmaceutically acceptable salt, a hydrate or a solvate thereof according to claim 1, wherein, X=P, "⌇" represents a single bond, $R_1$ and $R_2$ each are independently selected from the group consisting of hydroxyl, methoxy, ethoxy, n-propoxy, isopropoxy, n-butoxy, isobutoxy, tert-butoxy, benzyloxy, phenylethoxy, 1-phenylpropoxy, 1-phenylbutoxy, fluoromethoxy, difluoromethoxy, trifluoromethoxy, chloromethoxy, dichloromethoxy, trichloromethyl, aminomethoxy, aminoethoxy, hydroxylmethoxy, hydroxylethoxy, nitromethoxy and nitroethoxy.

4. The compound, or a pharmaceutically acceptable salt, a hydrate or a solvate thereof according to claim 1, wherein, X=P, "⌇" represents a single bond, $R_1$ and $R_2$ each are independently selected from the group consisting of hydroxyl, methoxy, ethoxy and benzyloxy.

5. The compound, or a pharmaceutically acceptable salt, a hydrate or a solvate thereof according to claim 1, wherein, when X=P, said pharmaceutically acceptable salt is an addition salt formed by the compound of Formula I and a base; or
when X=S, said pharmaceutically acceptable salt is an addition salt formed by the compound of Formula I and an acid.

6. The compound, or a pharmaceutically acceptable salt, a hydrate or a solvate thereof according to claim 1, selected from the group consisting of:
Compound 1: dibenzyl 2-(5-nitrothiazol-2-yl-carbamoyl)phenyl phosphate;
Compound 2: 2-(5-nitrothiazol-2-yl-carbamoyl)phenyl dihydrogen phosphate;
Compound 3: 2-(5-nitrothiazol-2-yl-carbamoyl)phenyl hydrogen phosphate monosodium salt;
Compound 4: 2-(5-nitrothiazol-2-yl-carbamoyl)phenyl phosphate disodium salt;
Compound 5: 2-(5-nitrothiazol-2-yl-carbamoyl)phenyl phosphate calcium salt;
Compound 8: 2-(5-nitrothiazol-2-yl-carbamoyl)phenyl 1-propanesulfonate;
Compound 9: 2-(5-nitrothiazol-2-yl-carbamoyl)phenyl 1-butanesulfonate;
Compound 12: 2-(5-nitrothiazol-2-yl-carbamoyl)phenyl taurate hydrochloride;
Compound 13: 2-(5-nitrothiazol-2-yl-carbamoyl)phenyl taurate
Compound 14: 2-(5-nitrothiazol-2-yl-carbamoyl)phenyl hydrogen phosphate monopotassium salt;
Compound 15: 2-(5-nitrothiazol-2-yl-carbamoyl)phenyl phosphate dipotassium salt;
Compound 16: 2-(5-nitrothiazol-2-yl-carbamoyl)phenyl hydrogen phosphate meglumine salt;
Compound 17: dimethyl 2-(5-nitrothiazol-2-yl-carbamoyl)phenyl phosphate; and
Compound 18: diethyl 2-(5-nitrothiazol-2-yl-carbamoyl)phenyl phosphate.

7. A pharmaceutical composition, comprising the compound of Formula I, or a pharmaceutically acceptable salt, a hydrate or a solvate thereof according to claim 1, and a-pharmaceutically acceptable carrier or excipient.

8. A method for preparing the compound of Formula I according to claim 1, wherein,
when X=P, the method comprises the following steps: in an aprotic solvent, in the presence of carbon tetrachloride and an organic base, and with dimethylaminopyridine (DMAP) as catalyst, tizoxanide is reacted with a compound of Formula II to obtain the compound of Formula I, and optionally, the compound of Formula I is reacted with a base to form a pharmaceutically acceptable salt; or

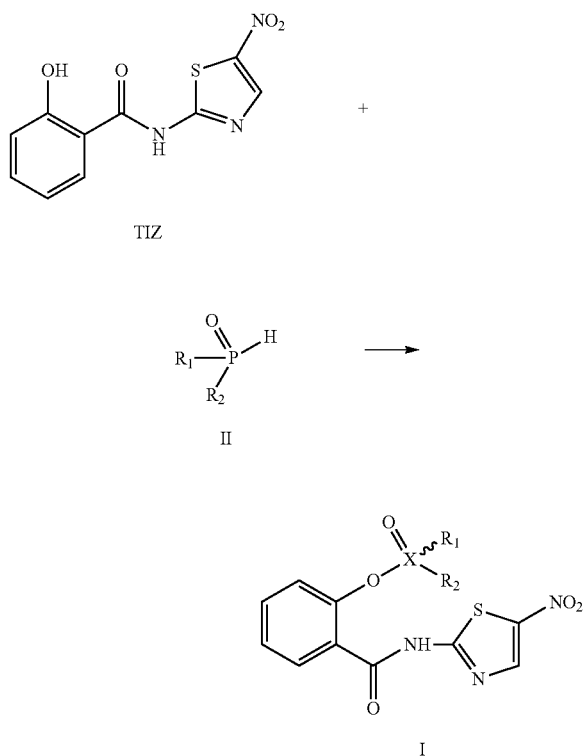

when X=S, the method comprises the following steps: tizoxanide is dissolved or suspended in an aprotic solvent, and with an organic base or an inorganic base as an acid receptor, is reacted with $R_2$-substituted sulfonyl chloride of Formula III, to obtain the compound of Formula I, and optionally, the compound of Formula I is reacted with an acid to form a pharmaceutically acceptable salt,

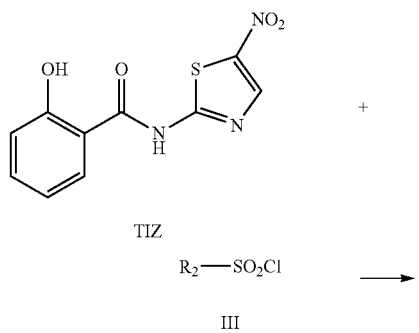

-continued

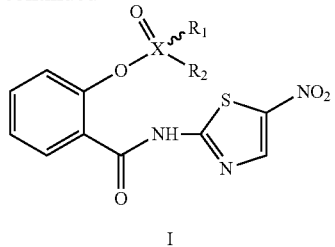

wherein said $R_1$ and $R_2$, as well as " ⌇ " have the same meanings as defined in claim 1.

9. A method for treating a disease in a mammal in need thereof, comprising administering to the mammal in need thereof a therapeutically effective amount of the compound of Formula I or a pharmaceutically acceptable salt, hydrate or solvate thereof according to claim 1, wherein the disease is selected from the group consisting of an infection by a parasite, Hepatitis B (HBV), Hepatitis C (HCV), influenza, a viral infectious disease caused by Rotavirus or Norovirus, and an infection caused by a bacterium, wherein
   the parasite is selected from the group consisting of *Giardia, Amoeba, Cryptosporidium, Cyclospora, Trichomonad, Encephalitozoon intestinalis, Isospora belli, Blastocystis hominis, Balantidium coli, Ascarislumbricoides, Enterocytozoon bieneusi,* Tapeworm, *Diplacanthus nanus, Giardia lamblia, Leishmania,* and *Fasciola hepatica,*
   the viral infectious disease caused by Rotavirus or Norovirus is a viral enterogastritis caused by a Rotavirus or a Norovirus,
   the infection caused by a bacterium is an infection caused by *Clostridium difficile, Tubercle bacillus* or *Helicobacter pylori.*

10. The compound of Formula I, or a pharmaceutically acceptable salt, a hydrate or a solvate thereof according to claim 1, wherein said halogen is F, Cl, Br or I.

11. The compound of Formula I, or a pharmaceutically acceptable salt, a hydrate or a solvate thereof according to claim 4, wherein,
   X=P, " ⌇ " represents a single bond, $R_1$ and $R_2$ each are independently selected from the group consisting of hydroxyl, methoxy and ethoxy.

12. The compound of Formula I, or a pharmaceutically acceptable salt, a hydrate or a solvate thereof according to claim 4, wherein,
   X=P, " ⌇ " represents a single bond, $R_1$ and $R_2$ are the same substituent, selected from the group consisting of hydroxyl, methoxy and ethoxy.

13. The compound, or a pharmaceutically acceptable salt, a hydrate or a solvate thereof according to claim 5, wherein,
   when X=P, said pharmaceutically acceptable salt is monosodium salt, disodium salt, calcium salt, monopotassium salt, dipotassium salt, or meglumine salt; or
   when X=S, said pharmaceutically acceptable salt is hydrochlorate, sulphate, acetate, or nitrate.

14. The pharmaceutical composition according to claim 7, wherein said pharmaceutical composition is in the form of a solid preparation, an injection, an external preparation, a spray, a liquid preparation, or a compound preparation.

15. The method according to claim 9, wherein said Tubercle bacillus is drug-resistant *Tubercle bacillus.*

16. The method according to claim 9, wherein said Tapeworm is *Taenia saginata* or *Hymenolepis nana.*

17. A method for inhibiting biofilm formation caused by a bacterium in a mammal in need thereof, comprising administering to the mammal in need thereof a therapeutically effective amount of the compound of Formula I, wherein the bacterium is *Staphylococcus epidermidis* or *Escherichia coli.*

18. The compound of Formula I, or a pharmaceutically acceptable salt, a hydrate or a solvate thereof according to claim 1, wherein,
   X=S, " ⌇ " represents a double bond, $R_1$ is O, and $R_2$ is selected from the group consisting of n-propyl, n-butyl and aminoethyl.

* * * * *